United States Patent [19]

Chow et al.

[11] Patent Number: 5,519,040
[45] Date of Patent: May 21, 1996

[54] SUBSTITUTED THIAZOLE SULFONAMIDES AS ANTIGLAUCOMA AGENTS

[75] Inventors: Ken Chow, Irvine; Michael E. Garst, Newport Beach; Judith M. Holmes, Santa Ana, all of Calif.

[73] Assignee: Allergan, Waco, Tex.

[21] Appl. No.: 236,720

[22] Filed: Apr. 29, 1994

[51] Int. Cl.$^6$ ............... C07D 277/36; A01K 31/425
[52] U.S. Cl. ............... 514/369; 514/252; 514/293; 544/369; 546/83; 548/166; 548/183; 548/186; 548/188
[58] Field of Search ............... 548/188, 186, 548/183, 166; 514/369, 252, 293; 544/369; 546/83

[56] References Cited

U.S. PATENT DOCUMENTS

| | | |
|---|---|---|
| 2,994,701 | 8/1961 | Sprague ............... 548/188 |
| 4,386,098 | 5/1983 | Woltersdorf, Jr. et al. . |
| 4,416,890 | 11/1983 | Woltersdorf, Jr. . |
| 4,426,388 | 1/1984 | Woltersdorf, Jr. . |
| 4,477,466 | 10/1984 | Shepard . |
| 4,486,444 | 12/1984 | Shepard . |
| 4,542,152 | 9/1985 | Shepard . |
| 4,544,667 | 10/1985 | Shepard et al. . |
| 5,300,499 | 4/1994 | Chow . |

OTHER PUBLICATIONS

Journal Of The American Chemical Society, vol. 72, No. 11, 17 Nov. 1950, pp. 4893–4896, W. Miller, "Heterocyclic sulfonamides as carbonic anhydrase inhibitors".

Journal Of Heterocyclic Chemistry, vol. 18, No. 5, Aug. 1981, pp. 997–1006, Cremlyn et al, "Some heterocyclic sulfonyl chlorides and derivatives".

*Primary Examiner*—Robert Gerstl
*Attorney, Agent, or Firm*—James M. Hoch; Robert J. Baran; Martin A. Voet

[57] ABSTRACT

The present invention provides novel carbonic anhydrase inhibitors represented by the structural formula:

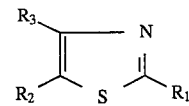

wherein

18 Claims, No Drawings

SUBSTITUTED THIAZOLE SULFONAMIDES AS ANTIGLAUCOMA AGENTS

BACKGROUND OF THE INVENTION

1. Field of the Invention

The present invention relates to substituted thiazole-sulfonamides that have carbonic anhydrase inhibition (CAI) activity and are useful as anti-glaucoma agents.

2. Background of the Art

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure, they also have other characteristics, e.g. membrane stabilizing activity, that are not acceptable for chronic ocular use. (S)-1-tert-Butylamino-3-[( 4-morpholino-1,2,5-thiadiazol-3-yl)oxy]- 2-propanol, a β-adrenergic blocking agent, was found to reduce intraocular pressure and to be devoid of many unwanted side effects associated with pilocarpine and, in addition, to possess advantages over many other [3-adrenergic blocking agents, e.g., to be devoid of local anesthetic properties, to have a long duration of activity, and to display minimal tolerance.

Although pilocarpine, physostigmine and the β-adrenergic blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such gross disruption of a basic enzyme system is justified only during an acute attack of alarmingly elevated intraocular pressure, or when no other agent is effective.

Topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof. Furthermore, U.S. Pat. No. 4,544,667 discloses a series of benzofuran-2-sulfonamides, and U.S. Pat. Nos. 4,477,466; 4,486,444; 4,542,152; and 4,585,787 disclose 5-phenylsulfonylthiophene-2-sulfonamides and 5-benzoylthiophene-2-sulfonamides and alkanoyloxy derivatives thereof which are reported to be topically effective carbonic anhydrase inhibitors useful in the treatment of elevated intraocular pressure (IOP) and glaucoma.

Additionally, U.S. Pat. No. 4,914,111 reports that thiophene or furan-2-sulfonamides, having a 4-benzyl substituent are effective for the topical treatment of elevated intraocular pressure and glaucoma. And another application assigned to Allergan by the same inventor (patent application Ser. No. 07/939,189, filed Jul. 2, 1992) describes the preparation and utility of 3-thiophenesulfonamide compounds in the treatment of elevated intraocular pressure (IOP) and glaucoma.

Finally, U.S. Pat. No. 2,994,701 discloses 2-sulfamyl-4-substituted thiazoles having diuretic activity on systemic administration.

In view of the above, it is clear that a great deal of research has been carried out on the use of sulfonamides for the topical treatment of glaucoma. However, the use of the substituted 2- and 5-thiazole sulfonamides has not been suggested for use in the topical treatment of glaucoma.

Therefore, one object of this invention is to provide novel substituted 2- and 5-thiazole sulfonamides.

It is another object of this invention to provide compounds having carbonic anhydrase inhibition activity.

Another object of this invention is to provide a method of inhibiting carbonic anhydrase activity to thereby treat elevated intraocular pressure (IOP) and glaucoma.

A further object of this invention is to provide CAI inhibitory compounds which have little or cysteine reactivity and hence little sensitization potential when administered to the eye.

Other objects and advantages of the instant invention will become apparent from a careful reading of the specification below.

SUMMARY OF THE INVENTION

The present invention provides novel compounds having carbonic anhydrase inhibition activity and useful in the treatment of glaucoma. These compounds are represented by the structural formula:

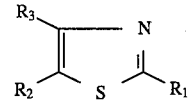

wherein $R_1$ is: $-SO_2NH_2$; $-S(O)_nR_4$; $-C(O)R_4$; $-OR_4$; phenyl, heteroaryl, aralkyl, heteroaralkyl, aralkenyl or heteroaralkenyl having from 5 to 6 atoms in the aryl moiety and 1 to 2 carbon atoms in the alkyl or 2 carbon atoms in the alkenyl moiety; alkyl having from 1 to 8 carbon atoms, or alkenyl or alkynyl having from 2 to 8 carbon atoms which can optionally be substituted with one or more hydroxy or carboxy groups wherein $R_4$ is: hydrogen; alkyl having from 1 to 6 carbon atoms or alkenyl or alkynyl having from 2 to 6 carbon atoms optionally substituted by dimethylamine; alicyclic having from 3 to 6 carbon atoms; carbalkoxyalkyl having 1 to 4 carbon atoms in the carbonyl moiety and from 1 to 6 carbon atoms in the alkoxy moiety; phenyl; $CH_3OCH_2OCH_2$; lower dialkylamino optionally further substituted by dimethylamine; or saturated nitrogen-containing heterocycles containing from 5 to 7 atoms optionally substituted with alkyl having from 1 to 3 carbon atoms and n is 0, 1 or 2;

$R_2$ is: $-SO_2NH_2$; $-S(O)_nR_4$; $-C(O)R_4$; $-OR_4$; bromo; chloro; aryl or heteroaryl having from 5 to 6 atoms; alkyl having from 1 to 8 carbon atoms, or alkenyl or alkynyl having from 2 to 8 carbon atoms which can optionally be substituted with one or more hydroxy groups wherein $R_4$ and n are as defined above;

$R_3$ is: hydrogen; alkyl of 1 to 6 carbon atoms; carboxy; lower carboxy alkyl; or phenyl optionally mono- or di-substituted with lower alkoxy, fluoro, chloro, bromo or alkyl of 1 to 3 carbon atoms; or $R_2$ and $R_3$ taken together form a ring fused with the 4–5 positions of the thiazole ring and are chosen from the group consisting of tetrahydrobenzene, tetrahydropyridine and thiopyran and can optionally be substituted by carboxylic acid, lower alkyl or benzyl esters of carboxylic acid, lower alkyl, or halogen; provided that at least one of $R_1$ and $R_2$ must represent the sulfonamide moiety, $-SO_2NH_2$.

These compounds when applied to the eye of a patient in need of such treatment reduce the elevated intraocular pressure of glaucoma and so can prevent or retard the sight-threatening sequelae of this condition.

DETAILED DESCRIPTION OF THE INVENTION

Definitions

Lower alkyl is accorded the meaning of 1 to 6 carbon aliphatic chains that are straight or branched, unless otherwise defined when used, in a similar fashion lower alkenyl or lower alkynyl are accorded the meaning of 2 to 6 carbon atom chains that are straight or branched.

A primary sulfonamide group is the sulfonamide moiety without substitution of the nitrogen atom attached to the $SO_2$ group, i.e. $-SO_2NH_2$.

A pharmaceutically acceptable salt may be prepared for any compound made in accordance with this invention, provided the compound has a functionality capable of forming such salt, for example an acid or an amine functionality.

A pharmaceutically acceptable salt may be any salt which retains the activity of the parent compound and does not impart any deleterious or untoward effect on the subject to which it is administered and in the context in which it is administered. Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di-, and trialkyl amines or ethanol amines. Salts may also be formed with caffeine, tromethamine and similar molecules. Where the nitrogen is sufficiently basic as to be capable of forming acid addition salts, such may be formed with any suitable inorganic or organic acids. Preferred salts are those formed with inorganic acids such as hydrochloric acid, sulfuric acid or phosphoric acid.

Abbreviations used in schemes 1, 2 and 3 below represent the following reagents or variables: n-BuLi=n-butyl lithium; NCS= N-chlorosuccinimide; $NH_4OH$=ammonium hydroxide; t-BuNH$_2$=tert. butylamine; Ac=acetate; Ac$_2$O=acetic anhydride; DMAP= dimethylamino pyridine; MeSO$_3$H= methanesulfonic acid; in RCHO, R can be phenyl or lower alkyl optionally substituted with hydroxy or silylated hydroxy; Jones oxidation is $CrO_3$ in pyridine; in RSSR, R can be phenyl or lower alkyl optionally substituted with hydroxy or silylated hydroxy; Oxone™=potassium peroxymonosulfate complex; Pd(Pϕ$_3$)$_2$Cl$_2$ =bis(tri-phenylphosphine) palladium chloride; Pd(Pϕ$_3$)$_4$= tetrakis(triphenylphosphine) palladium (O); NEt$_3$= triethylamine; CuI= copper (I) iodide; NaIO$_4$=sodium periodate; and 10% Pd on C=10% palladium on carbon, TBDMSCl=tertiary butyldimethylsilyl chloride.

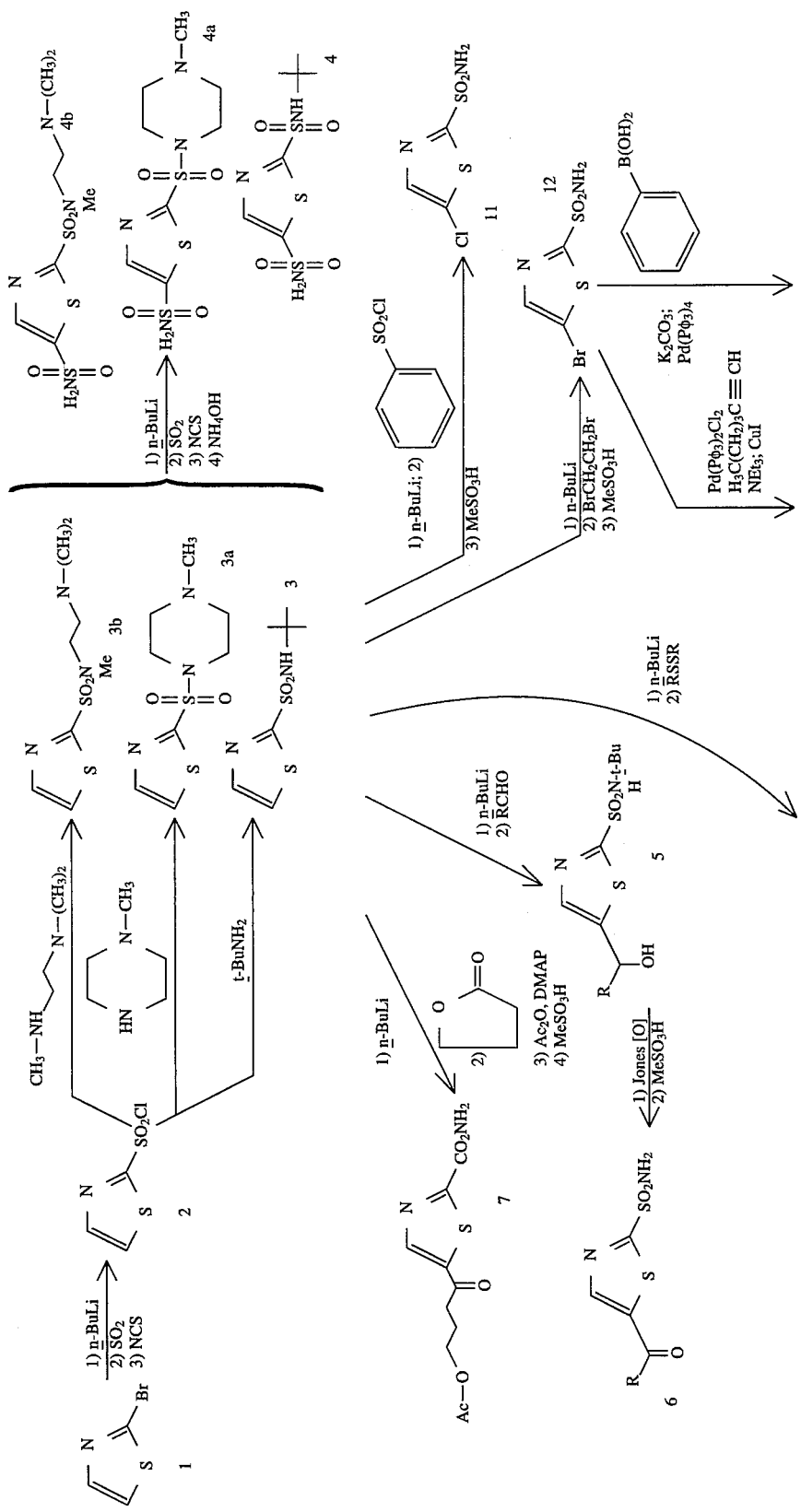

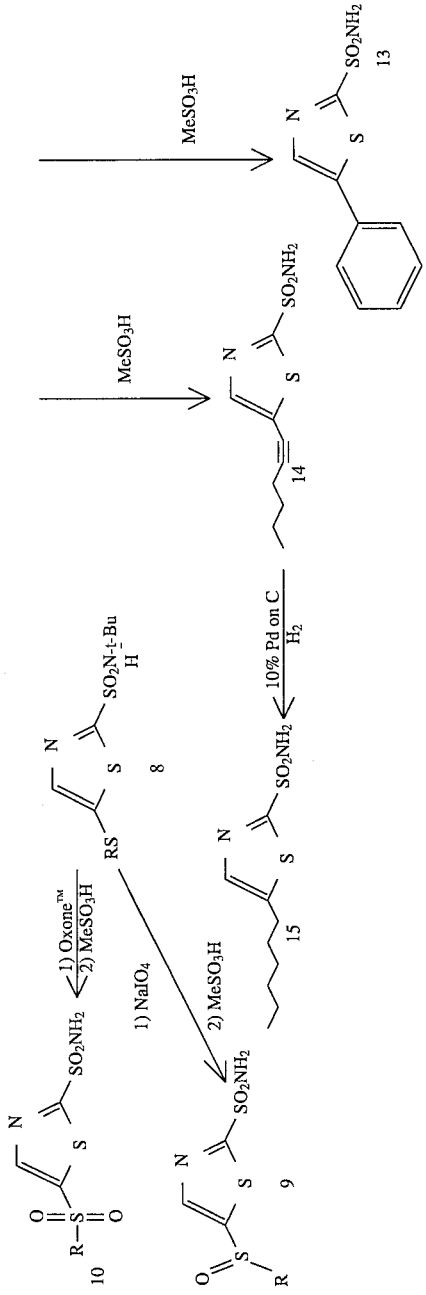

Scheme 2
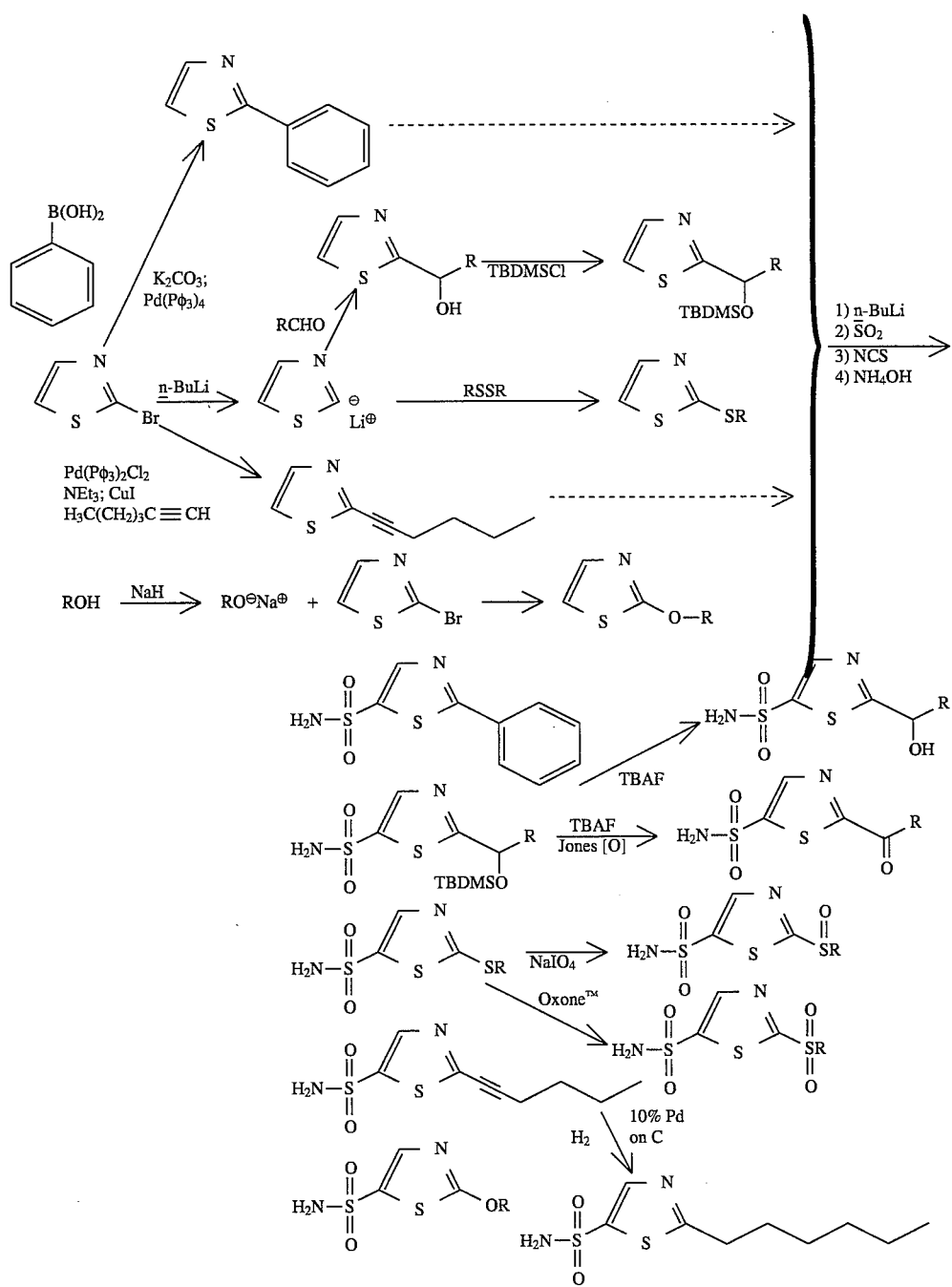
Scheme 3
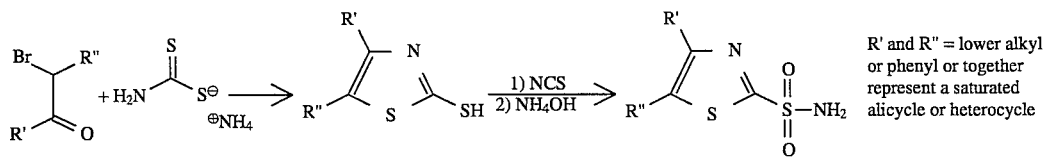
R' and R" = lower alkyl or phenyl or together represent a saturated alicycle or heterocycle -continued
Scheme 3

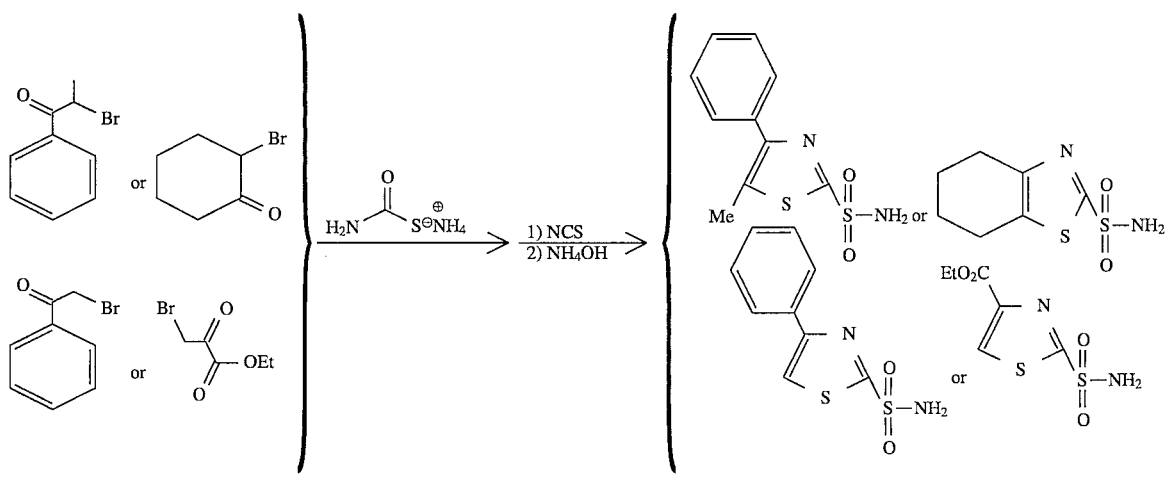

Specific Embodiments

The novel compounds of the invention may be prepared by the methods outlined in the preceding schemes, 1, 2 and 3.

In the formation of 2-sulfonamido-5-thiazole sulfonamides as shown in Scheme 1, 2-bromothiazole (1) is reacted with n-BuLi in tetrahydrofuran at a temperature of about −78° C. Into this solution containing the lithio-thiazole anion is then added sulfur dioxide gas ($SO_2$) at the same reduced temperature. After the sulfinate salt is formed, and warming to room temperature, the solvent is removed, and the residue is resuspended in dichloromethane at ambient temperature and N-chlorosuccinimide is added to form the 2-thiazole sulfonyl chloride (2). The 2-thiazole sulfonyl chloride (2), which can be isolated in crude form after filtration and stripping off solvent, can be reacted with a variety of alkyl amines or secondary nitrogen containing heterocycles to form substituted sulfonamides as shown in the next step of Scheme 1, such as 2(N-t-butylsulfamyl)-thiazole sulfonamide (3) and related compounds (3a and 3b).

Treatment of the N-substituted 2-thiazole sulfonamides (3, 3a, 3b) with n-BuLi, in tetrahydrofuran at about −78° C. gives the 5-lithio thiazole anion which when treated with sulfur dioxide gas ($SO_2$) at the same reduced temperature forms another sulfinate salt. After warming to room temperature, the solvent is removed, and the residue is resuspended in dichloromethane at ambient temperature and N-chlorosuccinimide is added to form the 5-thiazole sulfonyl chloride intermediate. Treatment of this intermediate compound with concentrated aqueous ammonium hydroxide yields the 5-sulfamyl compounds which correspond to 4, 4a, 4b.

2(N-t-butylsulfamyl)-thiazole sulfonamide (3) is useful as an intermediate in preparing 5-substituted 2-thiazole sulfonamides by a variety of electrophilic addition reactions. The lower half of Scheme 1 illustrates some of the reactions that are encompassed in this class of addition reactions. Reaction of 2(N-t-butylsulfamyl)-thiazole sulfonamide (3) with n-BuLi, in tetrahydrofuran at about −78° C. generates the 5-lithio thiazole anion which is reactive with a variety of electrophiles in the same low temperature range, including aldehydes, disulfides and γ-butyrolactone. Reaction of 3 with an aldehyde gives a hydroxy compound 5 which can be converted to the primary sulfonamide by elimination of 2-methylpropene in a halogenated polar solvent with a boiling point between 75° C. and 120° C. with methanesulfonic acid or another strong organic acid. Alternatively, the hydroxy compound 5 can be oxidized to a ketone by treatment with Jones reagent or a similar oxidizing agent, and similarly the protecting t-butyl group can be removed from the sulfonamide moiety by treatment with methanesulfonic acid at reflux in a high boiling point halogented solvent to give compounds of formula 6.

Reaction of 5-lithio thiazole anion with disulfides in tetrahydrofuran at about −78° C. affords the sulfide products represented by structure 8, which can generate the primary sulfonamide moiety by reflux in dichloromethane with methanesulfonic acid or another strong organic acid. Treatment of 8 with a mild oxidizing agent such as sodium periodate in a polar, protonated solvent, such as water at ambient temperature yields the sulfinate compounds (after removal of the t-butyl group by the standard method) corresponding to 9. Treatment of 8 with a stronger oxidizing agent such as Oxone™ (potassium peroxymonosulfate complex) in a polar, protonated solvent, such as water, or a water and ethanol mixture, at ambient temperature yields the sulfone compounds (after removal of the t-butyl group by the standard method) corresponding to 10.

Reaction of 5-lithio thiazole anion with γ-butyrolactone in tetrahydrofuran at about −78° C. gives the acylated product, 5-(4-hydroxybutanoyl)-2-thiazole sulfonamide the hydroxy function of which can be acetylated with acetic anhydride to provide the product 7, after elimination of the t-butyl group.

The 5-lithio thiazole anion can also be used to generate the 5-bromo (and chloro)-2-thiazole sulfonamides (11, 12) by reaction with suitable halogen sources such as benzenesulfonyl chloride or dibromoethane.

The brominated 2-thiazole sulfonamide is a useful intermediate in the formation of other 5-substituted compounds by catalyzed linking reactions. Reaction of 12 with phenyl boronic acid in the presence of tetrakis(triphenylphosphine) palladium(O) and potassium carbonate yields the 5-phenyl substituted compound, 13. And the catalyzed reaction of 12 and hexyne in the presence of bis(triphenylphosphine)palladium chloride with cuprous iodide and triethylamine provides the 5-hexynyl substituted compound, 14, which can subsequently be reduced to the 6-hexyl group, 15, using hydrogen and 10% palladium on carbon.

Scheme 2 outlines methods of making 2-substituted-5-thiazole sulfonamides which are analogous to the methods outlined in scheme 1 for making 5-substituted-2- thiazole sulfonamides. The same reagents and substantially the same starting materials are employed, only the order of introduction of substituents is altered. Starting with the 2-bromothiazole, the electrophilic addition of the variable substituent is effected first, and thereafter treatment of these 2-substituted intermediates with n-butyl lithium, sulfur dioxide, N-chlorosuccinimide, and ammonium hydroxide provides the sulfonamide moiety at the 5 position of the thiazole ring.

Scheme 3 demonstrates the method of making 4-substituted, 4 and 5-substituted, and the fused-ring compounds of the invention. Generally, these compounds can be synthesized by the cyclization of an α-bromo ketone compound with ammonium dithiocarbamate. The cyclized intermediate produced is the 4, or 4 and 5 substituted 2-thiazole thiol. Oxidation of the thiol with N-chlorosuccinimide and treatment of with concentrated ammonium hydroxide yields representative compounds of the reaction such as 4-phenyl-5-methyl-2-thiazole sulfonamide (16), 2-sulfamyl- 4,5,6,7-tetrahydrobenzothiazole (17), 4-phenyl- 2-thiazole sulfonamide (18) and 2-sulfamyl-4-carboxyethylthiazole (19).

In terms of inhibition activity of the carbonic anhydrase enzyme, preferred compounds of the invention are the 5-substituted- 2-thiazole sulfonamides and the 2-substituted-5-thiazole sulfonamides where the substituents are as described in the Summary of the Invention. Inhibition activities of examples of compounds of the invention can be seen in Table 1, below. Particularly preferred are those compounds that have an $IC_{50}$ (concentration at which 50% of enzyme is inhibited) value of 15 or less.

An additional measurement made on some compounds of the invention is the cysteine reactivity. This reactivity measurement gives an indication of the likelihood that a compound will react with cysteine residues in the eye, and so is a measure of the likelihood of development of sensitization in the eye to that compound. More particularly preferred are those compounds which exhibit little or no cysteine reactivity. In general, substituents that are more highly electron withdrawing, such as sulfonyl or carbonyl moieties adjacent to the thiazole ring, increase cysteine reactivity. Still more particularly preferred are those compounds with an $IC_{50}$ of 15 or less that also are not cysteine reactive, or have low cysteine reactivity.

When administered for the treatment of elevated intraocular pressure of glaucoma, the active compound is most desirably administered topically to the eye, although systemic treatment is also satisfactory.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

The active drug of this invention is most suitably administered in the form of ophthalmic pharmaceutical compositions adapted for topical administration to the eye such as a suspension, ointment, or as a solid insert. Formulations of these compounds may contain from 0.01 to 15% and especially 0.5% to 3% of medicament. Higher dosages as, for example, about 10%, or lower dosage can be employed provided the dose is effective in reducing or controlling elevated intraocular pressure. As a unit dosage from 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

The herein before described dosage values are believed accurate for human patients and are based on the known and presently understood pharmacology of the compounds, and the activity of other similar entities in the human eye. As with all medications, dosage requirements are variable and must be individualized on the basis of the disease and the response of the patient.

The pharmaceutical preparation which contains the active compound may be conveniently admixed with a non-toxic pharmaceutical organic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols, antibacterial components such as quaternary ammonium compounds, phenylmercuric salts known to have cold sterilizing properties and which are non-injurious in use, thimerosal, methyl and propyl paraben, benzyl alcohol, buffering ingredients such as sodium chloride, sodium borate, sodium acetate, and other conventional ingredients such as sorbitan monolaurate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert.

While many patients find liquid medication to be entirely satisfactory, others may prefer a solid medicament that is topically applied to the eye, for example, a solid dosage form that is suitable for insertion into the cul-de-sac. To this end the carbonic anhydrase inhibiting agent can be included with a non-bioerodable insert, i.e., one which after dispensing the drug remains essentially intact, or a bioerodable insert, i.e., one that either is soluble in lachrymal fluids, or otherwise disintegrates.

For example, one may use a solid water soluble polymer as the carrier for the medicament. The polymer used to form the insert may be any water soluble non-toxic polymer, for example, cellulose derivatives such as methylcellulose, sodium carboxymethyl cellulose, or a hydroxy lower alkyl cellulose such a hydroxyethyl cellulose, hydroxypropyl cellulose, hydroxypropylmethyl cellulose and the like; acrylates such as polyacrylic acid salts, ethyl acrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymers.

The invention is further illustrated by the following examples which are illustrative of a specific mode of practicing the invention and is not intended as limiting the scope of the appended claims.

Example 1:

2-N-t-butyl thiazole sulfonamide (3)

To a solution of 2-bromothiazole (9.1 g, 56 mmol) in 224 mL of ethyl ether, cooled to −78° C., was added dropwise n-butyllithium (1.6M, 34.7 mL, 56 mmol). The solution was stirred under argon at −78° C. for 60 min. An excess of SO$_2$ was bubbled through the reaction. The reaction was slowly warmed to room temperature and then concentrated under reduced pressure. The crude product was added to 224 mL of dichloromethane. N-chlorosuccinamide (8.2 g, 61.6 mmol) was added and the reaction stirred at room temperature for 3 min. The mixture was filtered and the filtrate collected and concentrated under reduced pressure. To the crude product in 130 mL of THF was added 30 mL of t-butylamine. The reaction was stirred at room temperature overnight and then diluted with water and extracted with ethyl acetate. The organic phase was washed with 1N HCl, water and then brine. The solvent was removed under reduced pressure and the product recrystallized from hexane/ethyl acetate. 7.5 g (34,3 mmol, 62%) of 2-N-t-butyl thiazole sulfonamide (white crystals) was recovered.

$^1$H NMR (CD$_3$)$_2$CO:
7.98 (d, J=3 Hz, 1H), 7.95 (d, J=3 Hz, 1H), 7.00 (bs, 1H), 1.28 (s, 9H)
$^{13}$C NMR (CD$_3$)$_2$CO:
169.48, 144.40, 125.71, 55.34, 30.04

Example 2:

2-Thiazole sulfonamide

To a solution of 2-N-t-butylthiazole sulfonamide (0.1 g, 0.45 mmol) in 5 mL of 1,2-dichloroethane was added methanesulfonic acid (69 mL, 1.1 mmol). The reaction was heated at reflux for 8 h and then concentrated under reduced pressure. The product was subjected to flash chromatography (1:1 hexane/ethyl acetate). 57 mg (0,35 mmol, 78%) of 2-thiazole sulfonamide (white solid) was recovered.

$^1$H NMR (CD$_3$)$_2$CO:
7.98 (d, J=3.1 Hz, 1H), 7.94 (d, J= 3.1 Hz, 1H), 7.26 (bs, 2H)
$^{13}$C NMR (CD$_3$)$_2$CO:
169,31, 144.69, 125.48
Mass Spect.:
EI-164 (M$^+$)
High Res.:
Calcd. 163.9214
Found 163.9221
Elemental Analysis:
Calcd. C 21.95, H 2.44, N 17.07
Found C 22.10, H 2.26, N 17.10

Example 3:

5-Benzoyl-2-thiazole sulfonamide

To a solution of 2-N-t-butylthiazole sulfonamide (0.5 g, 2.3 mmol) in 23 mL of ethyl ether, cooled to −78° C., was added n-butyllithium (1.26M, 3.65 mL, 4.6 mmol). The reaction was stirred under argon at −78° C. for 1 h. Benzaldehyde (0.26 mL, 2.53 mmol) was added and the reaction was stirred at room temperature (rt) overnight. Saturated ammonium chloride was added to quench the reaction. The mixture was extracted with ethyl acetate and the organic phase washed with water (3X) followed by brine. The solvent was removed under reduced pressure and the product subjected to flash chromatography (2:1 hexane/ethyl acetate). 0.35 g of the benzhydrol compound and 0.19 g of 2-N-t-butylthiazole sulfonamide were recovered.

To a solution of the benzhydrol compound (0.1 g, 0.31 mmol) in 3 mL of acetone was added Jone's reagent (2.67M, 0.12 mL, 0.31 mmol). The reaction was stirred at room temperature (rt) for 5 min and then quenched with isopropyl alcohol. The mixture was diluted with water and extracted with ethyl acetate. The organic phase was washed with water followed by brine. The solvent was removed under reduced pressure to afford 94 mg of the benzoyl compound.

To a solution of the benzoyl compound (0.1 g, 0.31 mmol) in 5 mL of 1,2-dichloroethane was added methanesulfonic acid (60 mL, 0.93 mmol). The reaction was heated at reflux for 2 h and then concentrated. The product was subjected to flash chromatography (3:2 hexane/ethyl acetate). 61 mg (0.23 mmol, 74%) of 5-benzoyl- 2-thiazole sulfonamide (white crystals) was recovered.

$^1$H NMR (CD$_3$)$_2$CO:
8.46 (s, 1H), 7.97–8.00 (m, 2H), 7.72–7.77 (m, 1H), 7.60–7.65 (m, 2H), 7.52 (bs, 2H)
$^{13}$C NMR (CD$_3$)$_2$CO:
187.26, 174.15, 149.28, 143.43, 137.76, 134.34, 130.07, 129.76
Mass Spect.:
EI-268 (M$^+$)
High Res.:
Calcd. 267.9976
Found 267.9968
Elemental Analysis:
Calcd. C 44.76, H 3.00, N 10.44
Found C 44.90, H 2.74, N 10.29

Example 4:

5-Chloro-2-thiazole sulfonamide (11)

To a solution of n-butyllithium (1.6M, 2.84 mL, 4.6 mmol) in 15 mL of ether at −78° C. was added 2-N-t-butylthiazole sulfonamide (0.5 g, 2.3 mmol) in 10 mL of ethyl ether. The reaction was stirred under argon at −78° C. for 1 h. Benzene sulfonyl chloride (0.30 mL, 2.3 mmol) was added and the reaction was stirred at rt for 30 min. Saturated ammonium chloride was added to quench the reaction. The solution was diluted with ethyl acetate and the organic phase washed with water (3X) followed by brine. The solvent was removed under reduced pressure and the product subjected to flash chromatography (5:1 hexane/ethyl acetate). 0.34 g of 5-chloro-2-N-t-butyl thiazole sulfonamide was recovered.

To a solution of 5-chloro-2-N-t-butyl thiazole sulfonamide (0.1 g, 0.40 mmol) in 10 mL of 1,2-dichloroethane was added methanesulfonic acid (78 mL, 1.2 mmol). The reaction was heated at reflux for 3 h and then concentrated. The product was subjected to flash chromatography (3:2 hexane/ ethyl acetate). 64 mg (0.3 mmol, 80%) of 5-chloro-2-thiazole sulfonamide (white crystals) was recovered.

$^1$H NMR (CD$_3$)$_2$CO:
7.94 (s, 1H), 7.39 (bs, 2H)
$^{13}$C NMR (CD$_3$)$_2$CO:
167.77, 143.22, 132.03
Mass Spect.:
EI-198 (M$^+$)
High Res.:
Calcd. 197.9324
Found 197.9318
Elemental Analysis:
Calcd. C 18.14, H 1.52, N 14.10
Found C 18.38, H 1.45, N 14.03

Example 5:

5-(Phenylthio)-2-thiazole sulfonamide

To a solution of n-butyllithium (1.6M, 1.7 mL, 2.8 mmol) in 25 mL of ether at −78° C. was added 2-N-t-butylthiazole sulfonamide (0.3 g, 1.4 mmol) in 5 mL of ethyl ether. The reaction was stirred under argon at −78° C. for 1 h. Phenyl disulfide (0.30 g, 1.4 mmol) in 5 mL of ethyl ether was added and the reaction was stirred at −78° C. for 30 min. Water was added to quench the reaction. The solution was diluted with ethyl acetate and the organic phase washed with water (3X) followed by brine. The solvent was removed under reduced pressure and the product subjected to flash chromatography (4:1 hexane/ethyl acetate). 0.20 g of 5-(phenylthio)-2-N-t-butyl thiazole sulfonamide and 0.06 g of 2-N-t-butylthiazole sulfonamide were recovered.

To a solution of 5-(phenylthio)-2-N-t-butyl thiazole sulfonamide (0.14 g, 0.43 mmol) in 10 mL of 1,2-dichloroethane was added methanesulfonic acid (84 mL, 1.29 mmol). The reaction was heated at reflux for 5 h and then concentrated. The product was subjected to flash chromatography (2:1 hexane/ethyl acetate). 97 mg (0.36 mmol, 84%) of 5-(phenylthio)-2-thiazole sulfonamide (off-white solid) was recovered.
$^1$H NMR $(CD_3)_2CO$:
8.05 (s, 1H), 7.34–7.44 (m, 7H)
$^{13}$C NMR $(CD_3)_2CO$:
172.12, 149.21, 136.25, 135.87, 130.76, 130.59, 129.05
Mass Spect.:
EI-273 (MH$^+$)
High Res.:
Calcd. 271.9748
Found 271.9745
Elemental Analysis:
Calcd. C 39.71, H 2.94, N 10.29
Found C 39.90, H 2.83, N 10.21

Example 6:

5-(Phenylsulfonyl)-2-thiazole sulfonamide

To a solution of 5-(phenylthio)-N-t-butyl thiazole sulfonamide (0.2 g, 0.61 mmol) (Example 5) in 6 mL of a 50% ethanol/water mixture was added oxone (0.6 g, 1.0 mmol) in 2 mL of water. The reaction was stirred at rt for 7 h and then quenched with sodium bicarbonate until the reaction becomes basic. The mixture was filtered and the filtrate concentrated. The product was subjected to flash chromatography (3:1 hexane/ethyl acetate). 0.18 g of 5-(phenylsulfonyl)-2-N-t-butyl thiazole sulfonamide was recovered.

To a solution of 5-(phenylsulfonyl)-2-N-t-butyl thiazole sulfonamide (0.10 g, 0.28 mmol) in 5 mL of 1,2-dichloroethane was added methanesulfonic acid (55 mL, 0.84 mmol). The reaction was heated at reflux for 2 h and then concentrated. The product was subjected to flash chromatography (2:1 hexane/ethyl acetate). 68 mg (0.22 mmol, 79%) of 5-(phenylsulfonyl)-2-thiazole sulfonamide (white crystals) was recovered.
$^1$H NMR $(CD_3)_2CO$:
8.54 (s, 1H), 8.10–8.13 (m, 2H), 7.68–7.82 (m, 3H), 7.55 (bs, 2H)
$^{13}$C NMR $(CD_3)_2CO$:
175.44, 148.90, 144.65, 141.74, 135.50, 130.87, 128.47
Mass Spect.:
EI-304 (M$^+$)
High Res.;
Calcd. 303.9646
Found 303.9671
Elemental Analysis:
Calcd. C 35.53, H 2.63, N 9.21
Found C 35.62, H 2.45,.N 9.13

Example 7:

5-(Ethylthio)-2-thiazole sulfonamide

To a solution of n-butyllithium (1.6M, 1.7 mL, 2.8 mmol) in 10 mL of ethyl ether at −78° C. was added 2-N-t-butylthiazole sulfonamide (0.3 g, 1.4 mmol) in 5 mL of ethyl ether. The reaction was stirred under argon at −78° C. for 1 h. Ethyl disulfide (0.18 mL, 1.4 mmol) was added and the reaction was stirred at rt for 30 min. Water was added to quench the reaction. The solution was diluted with ethyl acetate and the organic phase washed with water (3X) followed by brine. The solvent was removed under reduced pressure and the product subjected to flash chromatography (3:1 hexane/ethyl acetate). 0.20 g of 5-(ethylthio)-2-N-t-butyl thiazole sulfonamide and 0.11 g of 2-N-t-butylthiazole sulfonamide were recovered.

To a solution of 5-(ethylthio)-2-N-t-butyl thiazole sulfonamide (0.17 g, 0.61 mmol) in 10 mL of 1,2-dichloroethane was added methanesulfonic acid (0.12 mL, 1.83 mmol). The reaction was heated at reflux for 6 h and then concentrated. The product was subjected to flash chromatography (2:1 hexane/ethyl acetate). 0.12 g (0.54 mmol, 89%) of 5-(ethylthio)-2-thiazole sulfonamide (white solid) was recovered.
$^1$H NMR $(CD_3)_2CO$:
7.88 (s, 1H), 7.27 (bs, 2H), 2.98 (q, J=7.3 Hz, 2H), 1.29 (t, J=7.3 Hz, 3H)
$^{13}$C NMR $(CD_3)_2CO$:
170.34, 147.66, 137.82, 32.74, 14.93
Mass Spect.:
EI-224 (M$^+$)
High Res.:
Calcd. 223.9748
Found 223.9722
Elemental Analysis:
Calcd. C 26.79, H 3.57, N 12.50
Found C 27.14, H 3.53, N 12.35

Example 8:

5-Ethylsulfinyl-2-thiazole sulfonamide

To a solution of sodium periodate (92 mg, 0.43 mmol) in 2.6 mL of water was added 5-(ethylthio)-2-N-t-butyl thiazole sulfonamide (0.1 g, 0.36 mmol). The reaction was stirred at rt for 48 h. The mixture was filtered and the filtrate concentrated. The product was subjected to flash chromatography (1:1 hexane/ethyl acetate). 0.1 g of 5-(ethylsulfinyl)-2-N-t-butyl thiazole sulfonamide was recovered.

To a solution of 5-(ethylsulfinyl)-2-N-t-butyl thiazole sulfonamide (0.10 g, 0.34 mmol) in 5 mL of 1,2-dichloroethane was added methanesulfonic acid (44 mL, 0.68 mmol). The reaction was heated at reflux for 3.5 h and then concentrated. The product was subjected to flash chromatography (1:5 hexane/ethyl acetate). 72 mg (0.30 mmol, 88%) of 5-ethylsulfinyl-2-thiazole sulfonamide (light yellow solid) was recovered.
$^1$H NMR $(CD_3)_2CO$:
8.24 (s, 1H), 7.48 (bs, 2H), 3.08–3.30 (m, 2H), 1.25 (t, J=7.6 Hz, 3H)
Mass Spect.:
CI-241 (MH$^+$)
High Res.:
Calcd. 239.9697
Found 239.9681
Elemental Analysis:

Calcd. C 25.00, H 3.33, N 11.67
Found C 25.36, H 3.32, N 11.07

Example 9:

5-(2-Hydroxyethyl)thio-2-thiazole sulfonamide

To a solution of 2-N-t-butylthiazole sulfonamide (1.0 g, 4.5 mol) in 40 mL of ethyl ether at −78° C. was added n-butyllithium (1.6M, 5.7 mL, 9.0 mmol). The reaction was stirred under argon at −78 ° C. for 60 min. (2-Dimethylt-butylsiloxy)ethyl disulfide (1.74 g, 4.5 mmol) was added and the reaction was stirred at rt for 90 min. Water was added to quench the reaction. The solution was diluted with ethyl acetate and the organic phase washed with water (3X) followed by brine. The solvent was removed under reduced pressure and the product subjected to flash chromatography (5:1 hexane/ethyl acetate). 0.80 g of 5-((2-dimethylt-butyl-siloxy ethyl)thio)-2-N-t-butyl thiazole sulfonamide was recovered.

To a solution of 5-(( 2-dimethyl-t-butylsiloxyethyl)thio)-2-N-t-butyl thiazole sulfonamide (0.25 g, 0.61 mmol) in 6 mL of 1,2-dichloroethane was added methanesulfonic acid (0.16 mL, 2.44 mmol). The reaction was heated at reflux for 4 h and then concentrated. The product was subjected to flash chromatography (2:1 hexane/ethyl acetate). 73 mg (0.32 mmol, 52%) of 5-(2-hydroxyethyl)thio-2-thiazole sulfonamide (clear colorless liquid) was recovered.

$^1$H NMR $(CD_3)_2CO$:
7.86 (s, 1H), 3.78 (t, J=10 Hz, 2H), 3.10 (t, J=10 Hz, 3H)
$^{13}$C NMR $(CD_3)_2CO$:
170.2, 147.7, 138.2, 61.1, 41.3

Example 10:

5-(4-acetoxybutanoyl)-2-thiazole sulfonamide (7)

To a solution of 2-N-t-butylthiazole sulfonamide (0.5 g, 2.3 mol) in 23 mL of THF at −78° C. was added n-butyllithium (1.6M, 2.9 mL, 4.6 mmol). The reaction was stirred under argon at −78° C. for 60 min. g-butyrolactone (0.16 mL, 2.3 mmol) in 10 mL of THF was added and the reaction was stirred at −78° C. for 15 min. and then slowly warmed to rt and stirred overnight. The reaction was acidified with 1N HCl and then washed with water (3X) followed by brine. The solvent was removed under reduced pressure and the product subjected to flash chromatography (1:3 hexane/ethyl acetate). 0.27 g of 5-( 4-hydroxybutanoyl)-2-N-t-butyl thiazole sulfonamide was recovered.

To a solution of 5-(4-hydroxybutanoyl)-2-N-t-butyl thiazole sulfonamide (0.27 g, 0.88 mmol) in 8.8 mL of THF were added pyridine (0.14 mL, 1.76 mmol), 4-dimethylamino pyridine (catalytic amount) and acetic anhydride (0.17 mL, 1.76 mmol). The reaction was stirred at rt for overnight and then quenched with water. The organic phase was washed with water (2X) followed by brine. The solvent was removed under reduced pressure and the product subjected to flash chromatography (1:1 hexane/ethyl acetate). 0.26 g of 5-( 4-acetoxybutanoyl)-2-N-t-butyl thiazole sulfonamide was recovered.

To a solution of 5-(4-acetoxybutanoyl)- 2-N-t-butyl thiazole sulfonamide (0.20 g, 0.57 mmol) in 11 mL of 1,2-dichloroethane was added methanesulfonic acid (75 mL, 2.44 mmol). The reaction was heated at reflux for 4 h and then concentrated. The product was subjected to flash chromatography (1:1 hexane/ethyl acetate). 78 mg (0.27 mmol, 47%) of 5-(4-acetoxybutanoyl)- 2-thiazole sulfonamide (white solid) was recovered.

$^1$H NMR $(CD_3)_2CO$: 8.66 (s, 1H), 7.47 (bs, 2H), 4.11 (t, J=6.4 Hz, 2H), 3.20 (t, J=7.1 Hz, 2 H), 2.04 (m, 2H), 1.96 (s, 3H)
$^{13}$C NMR $(CD_3)_2CO$:
192.97, 173.95, 176.94, 147.98, 144.08, 63.79, 36.90, 23.76, 20.70
Mass Spect.:
CI-293 (MH$^+$)
High Res.:
Calcd. 292.0187
Found 309.0460 (+NH$_3$)
Elemental Analysis:
Calcd. C 36.99, H 4.11, N 9.59
Found C 37.15, H 4.27, N 9.29

Example 11:

4-Methyl-2-thiazole sulfonamide

To a solution of 4-methyl thiazole (3.0 g, 0.03 mol) in 300 mL of ether at −78° C. was added n-butyllithium (1.6M, 1.7 mL, 2.8 mmol). The reaction was stirred under argon at −78° C. for 30 min. An excess of $SO_2$ was bubbled through the reaction. The reaction was slowly warmed to rt and then concentrated under reduced pressure. The crude product was added to 300 mL of dichloromethane. N-chlorosuccinamide (4.41 g, 0.033 mol) was added and the reaction stirred at rt for 20 min. The mixture was filtered and the filtrate collected and concentrated under reduced pressure. To the crude product in 250 mL of acetone was added of concentrated ammonium hydroxide in 50 mL of acetone. The reaction was diluted with water and extracted with ethyl acetate. The organic phase was washed with water (3X) and then brine. Recrystallization from hexane/ethyl acetate afforded 2.13 g (12 mmol, 40%) of 4-methyl- 2-thiazole sulfonamide (tan crystals).

$^1$H NMR $(CD_3)_2CO$:
7.47 (s, 1H), 7.16 (bs, 2H), 2.44 (s, 3H)
$^{13}$C NMR $(CD_3)_2CO$:
168.01, 155.10, 120.00, 16.93
Mass Spect.:
EI-179 (MH$^+$)
High Res.:
Calcd. 177.9871
Found 177.9870
Elemental Analysis:
Calcd. C 26.97, H 3.37, N 15.73
Found C 27.01, H 3.24, N 15.74

Example 12:

5-Bromo-2-thiazole sulfonamide (12)

To a solution of 2-N-t-butylthiazole sulfonamide (0.1 g, 0.45 mmol) in 10 mL of THF, cooled to −78° C., was added n-butyllithium (1.6M, 0.57 mL, 0.9 mmol). The reaction was stirred under argon at −78° C. for 1 h. 1,2-dibromoethane (0.7 mL, 8.1 mmol) was added and the reaction stirred at rt overnight. The solvent was removed under reduced pressure and the product subjected to flash chromatography (4:1 hexane/ethyl acetate). 50 mg of 5-bromo-2-N-t-butylthiazole sulfonamide and 63 mg of 2-N-t-butylthiazole sulfonamide were recovered.

To a solution of 5-bromo-2-N-t-butylthiazole sulfonamide (50 mg, 0.17 mmol) in 2.5 mL of 1,2-dichloroethane was added methanesulfonic acid (22 mL, 0.34 mmol). The reaction was heated at reflux for 75 min and then concentrated. The product was subjected to flash chromatography (2:1 hexane/ethyl acetate). 38 mg (0.16 mmol, 94%) of 5-bromo-2-thiazole sulfonamide (white solid) was recovered.

$^1$H NMR (CD$_3$)$_2$CO:
8.02 (s, 1H), 7.39 (bs, 2H)
$^{13}$C NMR (CD$_3$)$_2$CO:
170.34, 146.4, 114.8
Mass Spect.:
EI-242 (M$^+$)
High Res.:
Calcd. 241.8819
Found 241.4424
Elemental Analysis:
Calcd. C 14.81, H 1.23, N 11.52
Found C 15.00, H 1.30, N 11.46

Example 13:

5-Methyl-4-phenyl-2-thiazole sulfonamide (16)

To a solution of ammonium dithiocarbamate (2.6 g, 0.024 mol) in 15 mL of ethanol was added 2-bromopropiophenone (5 g, 0.024 mol). The reaction was stirred at rt overnight. The next morning the reaction was heated at 70° C. for 6.5 h. The reaction was diluted with water and the mixture filtered. The solid was recrystallized from ethanol/water to recover 1.35 g of 5-methyl-2-mercapto-4-phenyl thiazole.

To a solution of 5-methyl-2-mercapto-4-phenyl thiazole (0.25 g, 1.2 mmol) in 18 mL of water/dichloromethane (1:3) was added N-chlorosuccinamide (0.64 g, 4.8 mmol). The reaction was stirred at rt for 45 min. and then diluted with water. The organic phase was washed with saturated sodium bicarbonate, water (2X) and then brine. The solvent was removed under reduced pressure and the crude product dissolved into 12 mL of acetone. 3 mL of concentrated ammonium hydroxide in 7 mL of acetone was added to the solution. The reaction was stirred at rt for 5 min. and diluted with water and extracted with ethyl acetate. The organic phase was washed with water (2X) followed by brine. The solvent was removed under reduced pressure and the product subjected to flash chromatography (2:1 hexane/ethyl acetate). A yellow solid was recovered which upon recrystallization from hexane/ethyl acetate afforded 0.16 g (0.63 mmol, 53%) of 5-methyl-4-phenyl- 2-thiazole sulfonamide (tan crystals).

$^1$H NMR (CD$_3$)$_2$CO:
7.70–7.72 (m, 2H), 7.41–7.51 (m, 3H), 7.26 (bs, 2H), 2.67 (s, 3H)
$^{13}$C NMR (CD$_3$)$_2$CO:
164.58, 152.74, 134.86, 134.82, 129.26, 129.11, 128.96, 12.85
Mass Spect.:
EI-254 (M$^+$)
High Res.:
Calcd. 254.0183
Found 254.0200
Elemental Analysis:
Calcd. C 47.24, H 3.94, N 11.02
Found C 47.13, H 3.82, N 10.99

Example 14:

2-Sulfamyl-4,5,6,7-tetrahydrobenzothiazole (17)

To a solution of ammonium dithiocarbamate (1.4 g, 12.4 mmol) in 25 mL of ethanol was added 2-bromocyclohexanone (2.2 g, 12.4 mmol). The reaction was stirred at rt overnight. The next morning the reaction was heated at 70° C. for 1 h. The solvent was removed under reduced pressure. The product was subjected to flash chromatography (3:1 hexane/ethyl acetate) to recover a yellow solid. Recrystallization from ethyl acetate afforded 0.54 g of 2-mercapto-4,5,6,7-tetrahydrobenzothiazole.

To a solution of 2-mercapto- 4,5,6,7-tetrahydrobenzothiazole (0.24 g, 1.4 mmol) in 21 mL of water/dichloromethane (1:2) was added N-chlorosuccinamide (0.75 g, 5.6 mmol). The reaction was stirred at rt for 30 min. and then diluted with water. The organic phase was washed with saturated sodium bicarbonate, water (2X) and then brine. The solvent was removed under reduced pressure and the crude product dissolved into 25 mL of acetone. 1 mL of concentrated ammonium hydroxide was added to the solution. The reaction was stirred at rt for 5 min. and diluted with water and extracted with ethyl acetate. The organic phase was washed with water (2X) followed by brine. The solvent was removed under reduced pressure and the product recrystallized from hexane/ethyl acetate to afford 82 mg (0.38 mmol, 27%) of 2-sulfamyl-4,5,6,7-tetrahydrobenzothiazole (tan crystals).

$^1$H NMR (CD$_3$)$_2$CO:
7.10 (bs, 2H), 2.74–2.87 (m, 4H), 1.85–1.89 (m, 4H)
$^{13}$C NMR (CD$_3$)$_2$CO:
165.00, 152.76, 135.59, 27.33, 23.96, 23.60, 23.25
Mass Spect.:
EI-218 (M$^+$)
High Res.:
Calcd. 218.0184
Found 218.0172
Elemental Analysis:
Calcd. C 38.53, H 4.59, N 12.84
Found C 38.54, H 4.62, N 12.84

Example 15:

5-(1-Hexynyl)-2-thiazole sulfonamide (14)

5-bromo-2-N-t-butylthiazole sulfonamide (0.57 g, 1.9 mmol), triethylamine (0.32 mL, 1.9 mmol), copper (I) iodide (91 mg, 0.48 mmol) and bistriphenylphosphine palladium chloride (67 mg, 0.095 mmol) were added to 19 mL of acetonitrile. The mixture was deoxygenated for 45 min. 1-hexyne was added and the reaction heated at 55°–60 ° C. for overnight. The next morning an additional 33 mg of bistriphenylphosphine palladium chloride and copper (I) iodide were added. The reaction was heated at 60° C. for 2 days. The solvent was removed under reduced pressure and the product subjected to flash chromatography (3:1 hexane/ethyl acetate) to afford N-t-butyl-5-(1-hexynyl)-2-thiazole sufonamide.

To a solution of N-t-butyl-5-(1-hexynyl)- 2-thiazole sufonamide in 19 mL of 1,2-dichloroethane was added methanesulfonic acid (0.25 mL, 0.34 mmol). The reaction was heated at reflux for 75 min and then concentrated. The product was subjected to flash chromatography (2:1 hexane/ethyl acetate). 88 mg of 5-bromo- 2-N-t-butylthiazole sulfonamide and 0.14 g (0.57 mmol, 30%) of 5-( 1-hexynyl)-2-thiazole sulfonamide (white crystals) was recovered.

$^1$H NMR (CD$_3$)$_2$CO:
7.95 (s, 1H), 7.31 (bs, 2H), 2.51 (t, J=7 Hz, 4H), 1.42–1.61 (m, 4H), 0.93 (t, J=7 Hz, 3H)
$^{13}$C NMR (CD$_3$)$_2$CO:
167.60, 147.40, 125.32, 101.41, 69.55, 30.90, 22.54, 19.64, 13.75
Mass Spect.:

EI-244 (M⁺)
High Res.:
Calcd. 244.0340
Found 244.0352
Elemental Analysis:
Calcd. C 44.26, H 4.92, N 11.48
Found C 44.45, H 5.07, N 11.39

Example 16:

5-Hexyl-2-thiazole sulfonamide (15)

To a solution of 5-(1-hexynyl)-2-thiazole sulfonamide (0.1 g, 0.41 mmol) in 7 mL of methanol was added 10% palladium/carbon (50 mg, 50 wgt %). The reaction was shaken at rt under 30 atm of hydrogen for 24 h. The next day the reaction was filtered through celite and the solvent removed under reduced pressure. $^1$H NMR indicated the alkynyl compound was still present. The product was redissolved in 7 mL of methanol and 100 mg of 10% palladium/carbon was added. The reaction was shaken at rt under 40 atm of hydrogen for 24 h. The next day the reaction was filtered through celite and the solvent removed under reduced pressure. The product was subjected to flash chromatography (3:1 hexane/ethyl acetate). 73 mg (0.29 mmol, 71%) of 5-hexyl-2-thiazole sulfonamide (white crystalline solid) was recovered.
$^1$H NMR (CD$_3$)$_2$CO:
7.69 (s, 1H), 1.66–1.71 (m, 2H), 1.29–1.40 (m, 8H), 0.87 (t, J=7 Hz, 3H)
$^{13}$C NMR (CD$_3$)$_2$CO:
166.78, 146.47, 141.71, 32.25, 32.02, 29.22, 27.21, 23.09, 14.21
Elemental Analysis:
Calcd. C 43.52, H 6.49, N 11.28
Found C 43.29, H 6.26, N 11.07

Example 17:

4-Phenyl-2-thiazole sulfonamide (18)

To a solution of ammonium dithiocarbamate (2.76 g, 25 mmol) in 50 mL of ethanol was added bromoacetophenone (5 g, 25 mmol). The reaction was stirred at rt overnight. The next morning the reaction was heated at 70° C. for 2.5 h. The reaction was diluted with water and extracted with ethyl acetate. The organic phase was washed with water (2X) followed by brine. The solvent was removed under reduced pressure. The product was dissolved in 375 mL of dichloromethane/water (2:1) and N-chlorosuccinamide (13.4 g, 100 mmol) was added. The reaction was stirred at rt for 60 min. and then diluted with water. The organic phase was washed with water (2X) followed by brine. The solvent was removed under reduced pressure and the crude product dissolved into 250 mL of acetone. 20 mL of concentrated ammonium hydroxide was added to the solution. The reaction was stirred at rt for 15 min. and then diluted with water and extracted with ethyl acetate. The organic phase was washed with water (2X) followed by brine. The solvent was removed under reduced pressure and the product subjected to flash chromatography (2:1 hexane/ethyl acetate). Recrystallization from ethyl acetate/hexane afforded 0.43 g (1.8 mmol, 7.2%) of 4-phenyl- 2-thiazole sulfonamide (white crystals).
$^1$H NMR (CD$_3$)$_2$CO:
8.24 (s, 1H), 8.00 (d, J=8 Hz, 2H), 7.37–7.50 (m, 5H)
$^{13}$C NMR (CD$_3$)$_2$CO:
169.18, 156.98, 134.33, 129.68, 129.60, 127.16, 118.93

Mass Spect.:
EI-240 (M⁺)
High Res.:
Calcd. 240.0027
Found 240.0029
Elemental Analysis:
Calcd. C 45.00, H 3.33, N 11.67
Found C 45.06, H 3.35, N 11.57

Example 18:

5-Phenyl-2-thiazole sulfonamide (13)

In 10 mL of deoxygenated toluene was added 5-bromo-2-N-t-butylthiazole sulfonamide (0.30 g, 1.0 mmol), phenylboronic acid (0.12 g, 1.0 mmol) and potassium carbonate (0.28 g, 2.0 mmol) in 1.5 mL of water/ethanol (2:1). The mixture was deoxygenated for 30 min.. Tetrakis(triphenylphosphine) palladium (O) was added and reaction heated at reflux for 36 h. The reaction was diluted with ethyl acetate and washed with water (2X) followed by brine. The solvent was removed under reduced pressure and the product subjected to flash chromatography (3:1 hexane/ethyl acetate) to afford N-t-butyl- 5-phenyl-2-thiazole sulfonamide.

To a solution of N-t-butyl-5-phenyl-2-thiazole sulfonamide (0.25 g, 0.84 mmol) in 17 mL of 1,2-dichloroethane was added methanesulfonic acid (0.11 mL, 1.68 mmol). The reaction was heated at reflux for 6.5 h and then concentrated. The product was subjected to flash chromatography (2:1 hexane/ethyl acetate). Recrystallization from ethyl acetate/hexane afforded 0.15 g (0.63 mmol, 63%) of 5-phenyl-2-thiazole sulfonamide (white crystals).
$^1$H NMR (CD$_3$)$_2$CO:
8.27 (s, 1H), 7.72–7.75 (m, 2H), 7.44–7.52 (m, 3H), 7.32 (bs, 2H)
$^{13}$C NMR (CD$_3$)$_2$CO:
167.54, 145.00, 140.32, 130.85, 130.27, 127.90
Mass Spect.:
EI-240 (M⁺)
High Res.:
Calcd.
Found
Elemental Analysis:
Calcd. C 45.00, H 3.33, N 11.67
Found C 44.91, H 3.29, N 11.52

Example 19:

5-(2-Carboxyethyl)thio-2-thiazole sulfonamide

To a solution of 2-N-t-butylthiazole sulfonamide (0.5 g, 2.3 mmol) in 23 mL of THF, cooled to 0° C., was added n-butyllithium (1.6M, 2.9 mL, 4.6 mmol). The reaction was stirred under argon at 0° C. for 30 min. Sulfur (74 mg, 2.3 mmol) was added and the reaction stirred at 0° C. for 1.5 h. The reaction was quenched with deoxygenated water and warmed to rt. 3-Bromopropionic acid (0.35 g, 2.3 mmol) and potassium carbonate (0.16 g, 1.15 mmol) in water were added to the reaction and stirred at rt overnight. The next day reaction was acidified with 1N HCl and extracted with ethyl acetate. The organic phase was washed with water (2X) followed by brine. The solvent was removed under reduced pressure and the product subjected to flash chromatography (15:1 dichloromethane/methanol). 0.31 g of 5-(2-carboxyethyl)thio- 2-N-t-butylthiazole sulfonamide was recovered.

To a solution of 5-(2-carboxyethyl)thio- 2-N-t-butylthiazole sulfonamide (0.15 g, 0.46 mmol) in 5 mL of 1,2-dichloroethane was added methanesulfonic acid (60 mL, 0.92 mmol). The reaction was heated at reflux for 2.5 h and then concentrated. The product was subjected to flash chromatography (5:1 chloroform/methanol). 60 mg (0.22 mmol, 48%) of 5-( 2-carboxyethyl)thio-2-thiazole sulfonamide (tan wax) was recovered.

$^1$H NMR $(CD_3)_2CO$:
7.90 (s, 1H), 7.28 (bs, 2H), 3.19 (t, J=7 Hz, 2H), 2.65 (t, J=7 Hz, 2H)
$^{13}$C NMR $(CD_3)_2CO$:
Elemental Analysis:
Calcd. C 26.86, H 3.00, N 10.44
Found C, H, N

Example 20:

5-(2-Carbomethoxyethyl)thio-2-thiazole sulfonamide

To a solution of 5-(2-carboxyethyl)thio-2-thiazole sulfonamide (42 mg, 0.16 mmol) in 5 mL of methanol was added a 1N HCl solution in ethyl ether. The solution was concentrated under reduced pressure to afford 26 mg (0.09 mmol,56%) of (white solid).

$^1$H NMR $(CD_3)_2CO$:
7.93 (s, 1H), 7.31 (bs, 2H), 3.63 (s, 3H), 3.19 (t, J=7 Hz, 2H), 2.70 (t, J=2H)
Elemental Analysis:
Calcd. C 29.78, H 3.57, N 9.92
Found C 30.08, H 3.46, N 9.75

Example 21:

5-Benzyloxycarbonyl-2-sulfamyl-4,5,6,7-tetrahydrothiazolo[5,4-c]pyridine

To a solution of ammonium dithiocarbamate (0.19 g, 1.7 mmol) in 2 mL of ethanol was added 1-benzyloxycarbonyl-3-bromo-4-piperidone (0.53 g, 1.7 mol). The reaction was stirred at rt overnight. The next morning the reaction was heated at 75° C. for 2 h. The reaction was diluted with ethyl acetate and washed with saturated sodium bicarbonate, water (2X) and then brine. The solvent was removed under reduced pressure and the product subjected to flash chromatography (2:1 hexane/ethyl acetate). Crystallization from ethyl acetate/hexane afforded 0.14 g of 5-benzyloxycarbonyl-2-mercapto- 4,5,6,7-tetrahydrothiazolo[5,4-c]pyridine.

To a solution of 5-benzyloxycarbonyl-2-mercapto- 4,5,6, 7-tetrahydrothiazolo[ 5,4-c]pyridine (0.14 g, 0.46 mmol) in 7.5 mL of water/dichloromethane (1:3) was added N-chlorosuccinamide (0.24 g, 1.84 mmol). The reaction was stirred at rt for 1 h and then diluted with water. The organic phase was washed with saturated sodium bicarbonate, water (2X) and then brine. The solvent was removed under reduced pressure and the crude product dissolved into 10 mL of acetone. 0.5 mL of concentrated ammonium hydroxide was added to the solution. The reaction was stirred at rt for 5 min. and diluted with water and extracted with ethyl acetate. The organic phase was washed with water (2X) followed by brine. The solvent was removed under reduced pressure and the product subjected to flash chromatography (1:1 hexane/ethyl acetate). 0.12 g (0.34 mmol, 74%) of 5-benzyloxycarbonyl-2-sulfamyl- 4,5,6,7-tetrahydrothiazolo[ 5,4-c]pyridine(white solid) was recovered.

$^1$H NMR $CD_3OD$:
7.32–7.37 (m, 5H), 5.17 (s, 2H), 4.90 (bs, 2H), 3.83–3.86 (m, 2H), 3.31 (bs, 2.89 (bs, 2H)
Elemental Analysis:
Calcd. C 47.58, H 4.28, N 11.89
Found C 48.10, H 4.23, N 11.29

Example 22:

2-Sulfamyl-4-carboxyethylthiazole (19)

Ethylbromopyruvate (7.1 mL, 56.8 mmol) was added to a slurry of ammonium dithiocarbamate (6.25 g, 56.8 mmol) in EtOH (35 mL). The solution was stirred at rt 18 h, then heated at 70°–80 ° C. for 2 h. The solution was cooled to 10° C. and water (70 mL) was added. The resulting precipitate was recrystallized from EtOH to give 0.7 g of 4-carboethoxy-2-mercapto thiazole. NCS (0.42 g, 3.17 mmol) was added to a solution of 4-carboethoxy-2-mercapto thiazole (0.15 g, 0.79 mmol) in $CH_2Cl_2$ (3.2 mL) and the solution layered with water (1.6 mL) and stirred for 2 h. The layers were separated and the water layer extracted with $CH_2 Cl_2$. The combined extracts were concentrated and the residue dissolved in acetone (1 mL) and $NH_4OH$ (1.6 mL) added. After 5 min the acetone was removed in vacuo and the residue taken up in water and extracted with EtOAc (6× 5 mL). The combined extracts were dried $(MgSO_4)$, filtered, concentrated and purified by chromatography using 35% EtOAc/hexane to give 0.1 g (54%) 4-carboethoxy-2-thiazole sulfonamide as a pale yellow solid.

$^1$H NMR $(CD_3)_2CO$: 8.65 (s, 1H), 7.43 (brs, 2H), 4.37 (q, 2H, J=7.0 Hz), 1.36 (t, 3H, J=7.0 Hz)
$^{13}$C NMR $(CD_3)_2CO$:
171.4, 162.4, 150.0, 134.4, 63.6, 16.0
Mass Spect.:
CI-237 (MH$^+$)
High Res.:
Calcd. $C_4H_5N_2O_4S_2$ 208.9690 (MH$^+$–$C_2H_4$)
Found 208.9676

Example 23:

5-Benzyl-2-thiazole sulfonamide

5-Benzyl-2-mercaptothiazole (0.5 g, 2.4 mmol) was dissolved in 9.6 mL of $CH_2Cl_2$ and NCS (1.33 g, 9.66 mmol) was added. The solution was layered with water (4.8 mL) and stirred at rt for for 2 hours. The material was extracted with $CH_2Cl_2$ and the organic layer washed with saturated $NaHCO_3$. The solvent was removed and the residue taken up in acetone (3 mL) and 5 mL $NH_4OH$ added. After 30 min. an additional 5 mL of $NH_4OH$ was added. After 30 minutes 10 mL of $NH_4OH$ was added. After hours 5 mL of $NH_4OH$ was added and the reaction stirred overnight. The acetone was removed and the aqueous extracted with ethyl acetate, dried $(MgSO_4)$, filtered and concentrated. The residue was subjected to flash chromatography (25% ethyl acetate/hexane) to afford 53 mg (9%) of 5-benzyl-2-thiazole sulfonamide.

$^1$H NMR $(CD_3)_2CO$:
7.77 (s, 1H), 7.33 (m, 4H), 7.28 (m, 1H), 7.14 (brs, 2H), 4.3 (s, 2H)
$^{13}$C NMR $(CD_3)_2SO$:
167.74, 145.85, 142.06, 140.26, 129.62, 129.30, 127.74, 33.21
Mass Spect.:
EI-254 (M$^+$)
High Res.:
Calcd. 254.0183

Found 254.0175
Elemental Analysis:
Calcd. C 47.23, H 3.96, N 11.01
Found C 47.03, H 3.82, N 11.85

Example 24:

4-(4-Methoxyphenyl)-2-thiazole sulfonamide (A)
5-Chloro-4-(4-methoxyphenyl)-2-thiazole sulfonamide (B)

4-(4-Methoxyphenyl)-2-mercaptothiazole (0.5 g, 2.24 mmol) was dissolved in 9 mL of $CH_2Cl_2$ and NCS (1.2 g, 8.97 mmol) was added. The solution was layered with water (4.5 mL) and stirred at rt for 2 hours. The material was extracted with $CH_2Cl_2$ and the organic layer washed with saturated $NaHCO_3$. The solvent was removed and the residue taken up in acetone (3 mL) and 5 mL $NH_4OH$ added. After 15 min. the acetone was removed and the aqueous extracted with ethyl acetate, dried ($MgSO_4$), filtered and concentrated. The residue was subjected to flash chromatography (25% ethyl acetate/hexane) to afford 0.20 g of 5-Chloro-4-(4-methoxyphenyl)-2-thiazole sulfonamide (B) and 40 mg of 4-(4-methoxyphenyl)-2-thiazole sulfonamide. (A)

(A)
$^1$H NMR $(CD_3)_2CO$:
8.06 (s, 1H), 7.92 (d, 2H, J=8.7 Hz), 7.32 (brs, 2H), 7.02 (d, J=8.7 Hz, 2H), 3.84 (s, 3H)
$^{13}$C NMR $(CD_3)_2SO$:
168.86, 161.15, 156.99, 128.56, 127.06, 116.94, 114.98, 55.62
Mass Spect.:
EI-271 $(MH^+)$
High RES.:
Calcd. 270.01328
Found 270.0145
Elemental Analysis:
Calcd. C 44.43, H 3.73, N 10.36
Found C 44.63, H 3.78, N 10.13
(B)
$^1$H NMR $(CD_3)_2CO$:
7.92 (d, 2H, J=9 Hz), 7.46 (brs, 2 H), 7.07 (d, J=9 Hz, 2H), 3.87 (s, 3H)
$^{13}$C NMR $(CD_3)_2SO$:
165.29, 161.34, 151.70, 130.54, 125.14, 123.98, 114.80, 55.71
Mass Spect.:
EI-305 $(MH^+)$
High RES.:
Calcd. 303.9743
Found 303.9761
Elemental Analysis:
Calcd. C 39.41, H 2.98, N 9.09
Found C 39.65, H 2.97, N 9.19

Example 25:

2-Thiophenyl-5-thiazole sulfonamide n-BuLi (2.0 mL, 3.2 mmol, 1.6M) was added dropwise to a −78° C. solution of 2-bromothiazole (0.05 g, 3.05 mmol) in dry $Et_2O$. After 1 h at −78° C., a solution of phenyldisulfide (0.7 g, 3.2 mmol) in dry $Et_2O$ (6 mL) was added slowly and the solution stirred 20 min. The reaction was quenched with water, the layers separated and the aqueous extracted with EtOAc (4×5 mL). The combined extracts were dried ($MgSO_4$), filtered and concentrated. The crude material was purified by flash chromatography using 5% EtOAc/hexane to give 0.41 g (69%) of 2-thiophenyl thiazole as a colorless oil.

n-BuLi (2.5 mL, 3.98 mmol, 1.6M) was added dropwise to a −78° C. solution of 2-thiophenyl thiazole (0.73 g, 3.8 mmol) in dry $Et_2O$ (10 mL). The solution turned dark brown after addition of the first few drops of n-BuLi. The solution was stirred 1 h at −78° C. then $SO_2$ gas was bubbled over the surface of the solution for 10 min. The solution was warmed to rt, then the solvent was removed and the residue taken up in $CH_2Cl_2$ (10 mL) and NCS (0.53 g, 3.98 mmol) was added. After stirring at rt for 2 h, another 1.06 g NCS was added and stirring continued another 1 h. The solution was filtered and the filtrate concentrated. The residue was dissolved in acetone (5 mL) and $NH_4OH$ (8 mL) was added. After 20 min, the acetone was removed in vacuo and the aqueous extracted with EtOAc, dried ($MgSO_4$) and concentrated. The crude material was purified using 35% EtOAc/hexane to give 0.28 g (27%) of 2-thiophenyl-5-thiazole sulfonamide as a pale yellow solid.
mp 134°–136° C.
$^1$H NMR $(CD_3)_2CO$:
7.96 (s, 1H), 7.79 (m, 2H), 7.61 (m, 3H), 7.03 (brs, 2H)
$^{13}$C NMR $(CD_3)_2CO$:
174.9, 146.1, 141.4, 136.1, 132.1, 131.4, 130.2
Elemental Analysis:
Calcd. C 39.72, H 2.96, N 10.29
Found C 39.33, H 2.59, N 9.97

Example 26:

2-Phenylsulfinyl-5-thiazole sulfonamide

A solution of $NaIO_4$ (0.55 g, 2.57 mmol) in water (5.7 mL) was added dropwise to a solution of 2-thiophenyl-5-thiazole sulfonamide (0.23 g, 0.86 mmol) in MeOH (14 mL) and the solution stirred 16 h. Dioxane (10 mL) was added to increase the solubility and the reaction stirred anther 48 h. The solution was filtered and the residue purified by flash chromatography using 30% EtOAc/hexane to give 0.3 g of 2-phenylsulfoxyl-5-thiazole sulfonamide.
mp 110°–112° C.
$^1$H NMR $(CD_3)_2CO$:
8.22 (s, 1H), 7.86 (m, 2H), 7.65 (m, 3H), 7.28 (br, 2H)
$^{13}$C NMR $(CD_3)_2CO$:
219.1, 182.8, 182.0, 179.8, 169.0, 166.4, 161.0
Mass Spect.;
288 $(M^+)$
High Res.:
Calcd. $C_9H_8N_2O_3S_3$ 287.9697 $(M^+)$
Found 287.9103
Elemental Analysis:
Calcd. C 37.49, H 2.80, N 9.71
Found C 37.77, H 2.96, N 9.44

Example 27:

2-Phenylsulfonyl-5-thiazole sulfonamide

A solution of Oxone (0.48 g, 0.77 mmol) in water (7 mL) was added dropwise to a solution of 2-thiophenyl thiazole (0.1 g, 0.5 mmol) in MeOH (7 mL) at rt. The solution was stirred at rt over night. The solution was cooled to 0° C. and saturated $NaHCO_3$ was added dropwise until the solution became basic. The solids were filtered off and washed with MeOH and EtOAc. The filtrate was evaporated, the residue taken up in a minimum volume of water and extracted with EtOAc. The combined extracts were dried ($Na_2SO_4$) and concentrated to give 0.11 g of 2-phenysulfonyl thiazole as a white powder.

n-BuLi (0.58 mL, 0.93 mmol, 1.6M) was added dropwise to a −78° C. solution of 2-phenylsulfonyl thiazole (0.2 g, 0.89 mmol) in dry THF (2 mL). The solution turned pale yellow after addition of the first few drops of n-BuLi. The solution was stirred for 1 h at −78° C. then $SO_2$ gas was bubbled over the surface of the solution for 10 min. The solution was warmed to rt, then the solvent was removed and the residue taken up in $CH_2Cl_2$ (2 mL) and NCS (0.12 g, 0.93 mmol) was added. After stirring at rt for 2 h, the solution was filtered and the filtrate concentrated. The residue was dissolved in acetone (2 mL) and $NH_4OH$ (2 mL) was added. After 20 min., the acetone was removed in vacuo and the aqueous extracted with EtOAc, dried ($MgSO_4$) and concentrated. The crude material was purified using 35% EtOAc/hexane to give 0.14 g (50%) of 2-phenylsulfonyl-5-thiazole sulfonamide as a pale yellow solid.
mp 119°–120° C.
$^1$H NMR $(CD_3)_2CO$:
8.33 (s, 1H), 8.12 (m, 1H), 7.85 (m, 1H), 7.74 (m, 2H), 7.44 (brs, 1H)
$^{13}$C NMR $(CD_3)_2CO$:
171.0, 148.6, 147.0, 138.8, 136.0, 130.7, 129.6,
Elemental Analysis:
Calcd. C 35.56, H 2.65, N 9.21
Found C 35.64, H 2.49, N 9.11

Example 28:

2-(1-Hydroxyhexyl)-5-thiazole sulfonamide n-BuLi (4.0 mL, 6.4 mmol, 1.6M) was added dropwise to a −78° C. solution of 2-bromothiazole (1.0 g, 6.1 mmol) in dry $Et_2O$ (12 mL). After stirring at −78° C. for 1 h, hexanal (0.77 mL, 6.4 mmol) was added and the solution stirred for 30 min. before a solution of TBDMSCl (1.1 g, 7.3 mmol) in dry $Et_2O$ (5 mL) was added. The solution was allowed to warm to rt while stirring for 16 h. The reaction was quenched with water, the layers separated and the aqueous extracted with EtOAc. The combined extracts were dried ($MgSO_4$) and condensed. The crude material was purified by flash chromatography using 30% EtOAc/hexane to give 0.70 g (62%) of 2-(1-hydroxyhexyl)thiazole.

TBDMSCl (1.37 g, 9.07 mmol) and DBU (1.4 mL, 9.07 mmol) were added to a solution of 2-(1-hydroxyhexyl)thiazole (0.7 g, 3.8 mmol) in dry THF (8 mL). The mixture was stirred at rt for 3 h, then quenched with water and the layers separated. The aqueous portion was extracted with EtOAc, the combined extracts dried ($MgSO_4$) and concentrated. The material was purified by flash chromatography to give 1.03 g (91%) of 2-(1-trimethylsiloxyhexyl)thiazole as a pale yellow oil.

n-BuLi (1.77 mL, 2.83 mmol, 1.6M) was added dropwise to a −78° C. solution of 2-(1-trimethylsiloxyhexyl)thiazole (0.81 g, 2.7 mmol) in dry THF (2 mL). The solution was stirred 1 h at −78° C., then $SO_2$ gas was bubbled over the surface of the solution for 10 min. The solution was warmed to rt, then the solvent removed and the residue taken up in $CH_2Cl_2$ (2 mL) and NCS (6.38 g, 2.83 mmol) was added. After stirring at rt for 2 h, the solution was filtered and the filtrate concentrated. The residue was dissolved in acetone (2 mL) and $NH_4OH$ (5.4 mL) was added. After 20 min, the acetone was removed in vacuo and the aqueous extracted with EtOAc, dried ($MgSO_4$) and concentrated. The crude material was dissolved in THF (5 mL) and TBAF (5 mL) was added. After 30 min. the reaction was quenched with water and the layers separated. The aqueous portion was extracted with EtOAc, the combined extracts dried ($MgSO_4$), concentrated and purified by flash chromatography using 40% EtOAc/hexane to give 0.43 g (60%) of 2-(1-hydroxyhexyl)-5-thiazole sulfonamide as a white solid.
mp 139°–141° C.
$^1$H NMR $(CD_3)_2CO$:
8.03 (s, 1H), 7.03 (brs, 2H), 5.46 (brd, 1H, J=4.5 Hz), 4.9 (m, 1H), 1.93 (m, 1H) 1.8 (m, 1H), 1.5 (m, 2H), 1.3 (m, 4 H), 0.87 (t, 3H, J=6.9 Hz)
$^{13}$C NMR $(CD_3)_2CO$:
183.7, 145.5, 141.5, 72.2, 38.5, 32.2, 25.2, 23.1, 14.2
Elemental Analysis:
Calcd. C 40.98, H 6.10, N 10.6
Found C 41.05, H 6.15, N 10.55

Example 29:

2-(1-Hexanoyl)-5-thiazole sulfonamide

Jones' reagent (0.14 mL, 0.38 mmol, 2.67M) was added dropwise to a 0° C. solution of 2-(1-hydroxyhexyl)- 5-thiazole sulfonamide (0.08 g, 0.32 mmol) in acetone (1 mL). The ice bath was removed and the solution stirred for 30 min. The reaction was quenched with a few drops of isopropanol and the acetone removed in vacuo. The residue was taken up in water and extracted with EtOAc. The combined extracts were dried ($MgSO_4$), concentrated and recrystallized from EtOAc/hexane to give 0.031 g (38%) of 2-(1-hexanoyl)-5-thiazole sulfonamide as a white solid.
mp 124°–125° C.
$^1$H NMR $(CD_3)_2CO$:
8.34 (s, 1H), 7.35 (brs, 2H), 3.15 (t, 2H, J=7.3 Hz), 1.73 (m, 2H), 1.37 (m, 4H), 0.89 (t, 3H, J=7.0 Hz)
$^{13}$C NMR $(CD_3)_2CO$:
194.5, 170.7, 148.3, 146.7, 38.6, 32.0, 24.1, 23.1, 14.1
Mass Spect.:
CI-263 (MH$^+$)
High Res.:
Calcd. $C_9H_{14}N_2O_3S_2$ 262.0445 (M$^+$)
Found 262.0454
Elemental Analysis:
Calcd. C 41.20, H 5.38, N 10.68
Found C 40.99, H 5.19, N 10.47

Example 30:

2-Ethylthio-5-thiazole sulfonamide n-BuLi (4.0 mL, 6.4 mmol, 1.6M) was added dropwise to a −78° C. solution of 2-bromothiazole (1.0 g, 6.1 mmol) in dry $Et_2O$ (12 mL). After 1 h at −78° C., ethyldisulfide (0.79 g, 6.4 mmol) was added slowly and the solution stirred for 16 h. The reaction was quenched with water, the layers separated and the aqueous extracted with EtOAc (4×5 mL). The combined extracts were dried ($MgSO_4$), filtered and concentrated. The crude material was purified by flash chromatography using 5% EtOAc/hexane to give 0.55 g (62%) of 2-thioethyl thiazole as a light yellow oil.

n-BuLi (1.6 mL, 2.52 mmol, 1.6M) was added dropwise to a −78° C. solution of 2-thioethyl thiazole (0.35 g, 2.4 mmol) in dry $Et_2O$ (8 mL). The solution was stirred for 1 h at −78° C., then $SO_2$ gas was bubbled over the surface of the solution for 10 min. The solution was warmed to rt, and the solvent removed. The residue taken up in $CH_2Cl_2$ ( 8 mL) and NCS (0.34 g, 2.52 mmol) was added. After stirring at rt 2 h, the solution was filtered and the filtrate concentrated. The residue was dissolved in acetone (8 mL) and $NH_4OH$ (5.0 mL) was added. After 5 min, the acetone was removed in vacuo and the aqueous extracted with EtOAc, dried (MgSO$_4$) and concentrated. The crude material was purified by flash chromatography using 35% EtOAc/hexane to give 0.29 g (53%) of 2-ethylthio-5-thiazole sulfonamide as a light brown solid.
mp 95°–96° C.
$^1$H NMR CDCl$_3$:
7.96(s, 1H), 7.09 (brs, 2H), 3.3 (q, 2H, J=7.2 Hz), 1.4 (t, 3H, J=7.2Hz)
$^{13}$C NMR CDCl$_3$:
172.0, 145.5, 140.2, 28.9, 14.6
Mass Spect.:
CI-224 (M$^+$)
High Res.:
Calcd. C$_5$H$_8$N$_2$O$_2$S$_3$ 223.9749 (M$^+$)
Found 223.9766
Elemental Analysis:
Calcd. C 26.77, H 3.59, N 12.49
Found C 27.02, H 3.47, N 12.53

Example 31:

2-Ethylsulfonyl-5-thiazole sulfonamide

A solution of Oxone (0.72 g, 1.17 mmol) in water (11 mL) was added dropwise to a solution of 2-thioethyl-5-thiazole sulfonamide (0.15 g, 0.78 mmol) in MeOH (11 mL) at rt. The solution was stirred at rt for 16 h. The solution was cooled to 0° C. and saturated NaHCO$_3$ was added dropwise until the solution became basic. The solids were filtered off and washed with MeOH and EtOAc. The filtrate was evaporated, the residue taken up in a minimum volume of water and extracted with EtOAc. The combined extracts were dried (Na$_2$SO$_4$), concentrated and purified by flash chromatography using 40% EtOAc/hexane to give 0.15 g of 2-ethylsulfonyl-5-thiazole sulfonamide as a white solid.
mp 129°–130° C.
$^1$H NMR (CH$_3$)$_2$CO: 8.43(s, 1H), 7.47 (brs, 2H), 3.59 (q 2H, J=7.2 Hz), 1.35 (t, 3H, J=7.2 Hz)
$^{13}$C NMR (CH$_3$)$_2$CO:
169.4, 148.6, 146.9, 49.8, 7.3
Elemental Analysis:
Calcd. C 23.43, H 3.15, N 10.93
Found C 23.64, H 3.03, N 10.92

Example 32:

2-(1-Ketocyclopropyl)-5-thiazole sulfonamide n-BuLi (26.7 mL, 42.8 mmol, 1.6M) was added dropwise to a –78° C. solution of 2-bromothiazole (6.7 g, 40.8 mmol) in dry Et$_2$O (80 mL). After stirring at –78° C. for 1 h, cyclopropanal (32 mL, 42.8 mmol) was added and the solution stirred 30 min. The reaction was quenched with water, the layers separated and the aqueous extracted with EtOAc. The combined extracts were dried (MgSO$_4$), and condensed. The crude material was purified by flash chromatography using 40% EtOAc/hexane to give 5.98 g (95%) of 2-(1-hydroxy- 1-cyclopropylmethyl)thiazole as a yellow oil.

TBDMSCl (3.5 g, 23.2 mmol) and DBU (3.5 mL, 23.2 mmol) were added to a solution of 2-(1-hydroxy- 1-cyclopropylmethyl)thiazole (3.0 g, 19.4 mmol) in dry THF (40 mL). The mixture was stirred at rt for 16 h, then quenched with water and the layers separated. The aqueous portion was extracted with EtOAc, the combined extracts dried (MgSO$_4$) and concentrated. The material was purified by flash chromatography using 5% EtOAc/hexane to give 4.97 g (95%) of 2-( 1-t-butyldimethylsiloxy-1-cyclopropylmethyl)thiazole as a colorless oil.

n-BuLi (1.22 mL, 1.95 mmol, 1.6M) was added dropwise to a –78° C. solution of 2-(1-t-butyldimethylsiloxy- 1-cyclopropylmethyl)thiazole (0.5 g, 1.86 mmol) in dry THF (18 mL). The solution was stirred for 1 h at –78° C., then SO$_2$ gas was bubbled over the surface of the solution for 10 min. The solution was warmed to rt, then the solvent was removed and the residue taken up in CH$_2$Cl$_2$ (18 mL) and NCS (0.26 g, 1.95 mmol) was added. After stirring at rt for 2 h, the solution was filtered and the filtrate concentrated. The residue was dissolved in acetone (10 mL) and NH$_4$OH (3.7 mL) was added. After 20 min., the acetone was removed in vacuo and the aqueous extracted with EtOAc, dried (MgSO$_4$) and concentrated. The crude material was dissolved in THF (10 mL) and TBAF (2.8 mL, 1.0M) was added. After 30 min. the reaction was quenched with water and the layers separated. The aqueous portion was extracted with EtOAc, the combined extracts dried (MgSO$_4$), concentrated and purified by flash chromatography using 60% EtOAc/hexane to give 0.33 g (76%) of 2-(1-hydroxy-1-cyclopropylmethyl)- 5-thiazole sulfonamide.

Jones' reagent (0.63 mL, 1.69 mmol, 2.67M) was added dropwise to a 0° C. solution of 2-(1-hydroxy- 1-cyclopropylmethyl)-5-thiazole sulfonamide (0.33 g, 1.4 mmol) in acetone (5 mL). The ice bath was removed and the solution stirred for 30 min. The reaction was quenched with a few drops of isopropanol and the acetone removed in vacuo. The residue was taken up in water and extracted with EtOAc. The combined extracts were dried (MgSO$_4$), concentrated and purified by flash chromatography using 30% EtOAc/hexane to give 0.23 g (72%) of 2-(1-ketocyclopropyl)-5-thiazole sulfonamide as a white solid.
mp 148°–149° C.
$^1$H NMR (CD$_3$)$_2$CO:
8.38 (s, 1H), 7.37 (brs, 2H), 3.19 (m, 1H), 1.21 (m, 4H)
$^{13}$C NMR (CD$_3$)$_2$CO:
194.0, 170.7, 148.2, 146.8, 14.5, 13.3
Mass Spect.:
High Res.:
Calcd. C$_7$H$_8$N$_2$O$_3$S$_2$ 231.9976 (M$^+$)
Found 231.9954
Elemental Analysis:
Calcd. C 36.20, H 3.47, N 12.06
Found C 35.89, H 3.34, N 11.97

Example 33:

2-(4-(N,N-dimethyl)aminobutanoyl)-5-thiazole sulfonamide

TMSCl (1.72 mmol, 0.22 mL) was added to a solution of NaI (1.72 mmol, 0.26 g) and 2-(1-ketocyclopropyl)- 5-thiazole sulfonamide (0.86 mmol, 0.2 g) in acetonitrile (2 mL). After stirring at rt for two hours, the reaction was still incomplete. The reaction was stirred overnight, NaI (0.26 g) and TMSCl (0.22 mL) were added. Reaction was completed after two hours. Saturated Na$_2$SO$_3$ was added and the mixture extracted with ethyl acetate (4x). The organic phases were combined, dried (MgSO$_4$), filtered and concentrated. The residue was subjected to flash chromatography (50% ethyl acetate/hexane) to afford 0.15 g (48%) of 2-(1-hydroxy-4-iodobutyl)- 5-thiazole sulfonamide.

TBSOTf (2.53 mmol, 0.58 mL), and pyridine (2.53 mmol, 0.2 mL) were precomplexed in THF (2 mL), then added to a solution of 2-(1-hydroxy-4-iodobutyl)-5- sulfonamide (1.2, 0.43 g). The reaction was stirred at rt for two hours. The reaction was quenched with water and extracted with ethyl acetate, dried (MgSO$_4$), filtered and concentrated. The residue was subjected flash chromatography (25% ethyl acetate/hexane) to afford 0.37 g (64%) of 2-(1-t-butyldimethylsiloxy- 4-iodobutyl)-5-thiazole sulfonamide.

Dimethylamine was bubbled through a solution of 2-(1-t-butyldimethylsiloxy-4-iodobutyl)-5-thiazole sulfonamide (0.78 mmol, 0.37 g ) in THF (8 mL) at 0° C. After 30 minutes the solvent was removed and the residue taken up in THF and TBAF (1.17 mmol) added. The reaction was stirred at rt for 2 hours. The reaction was concentrated and the residue subjected to flash chromatography (5% MeOH/NH$_3$/CHCl$_3$) to afford 0.16 g (72%) of 2-(1-hydroxy-4-(N,N-dimethylamino)butyl)-5-thiazole sulfonamide.

A mixture of 2-(1-hydroxy- 4-(N,N-dimethylamino)butyl)-5-thiazole sulfonamide (0.35 mmol, 0.098 g) and MnO$_2$ (5.27 mmol, 0.46 g) in THF was stirred at rt overnight. The mixture was filtered through celite and the solvent removed. The residue was subjected to flash chromatography (10% MeOH/NH$_3$/CHCl$_3$) to afford 34.4 mg ( 35%) of 2-(1-keto-4-(N,N-dimethylamino)butyl)- 5-thiazole sulfonamide.

2-(4-(N,N-dimethylamino)butanoyl)-5-thiazole sulfonamide (34.4 mg) was stirred with 4 mL of an ethereal solution of HCl. After 2 hours the solvent was removed and the solid left under vacuum.
mp 202°–203° C. (decomposed)
$^1$H NMR (CD$_3$)$_2$SO:
8.43 (s, 1H), 8.21 (brs, 2H), 3.24 (t, 2H, J=7.9 Hz), 3.12 (m, 2H), 2.78 (s, 6H), 2.0 (m, 2H)
Elemental Analysis:
Calcd. C 34.44, H 5.14, N 13.39
Found C 34.05, H 5.02, N 12.98

Example 34:

2-(1-Butoxy)-5-thiazole sulfonamide

A suspension of NaH (6.7 mmol, 0.27 g, 60% dispersion) in dry DMF was stirred with butanol (6.09 mmol, 0.55 mL) under argon until evolution of hydrogen ceased. 2-Bromothiazole (6.09 mmol, 0.55 mL) was added and after 15 minutes the mixture was heated to reflux. After 48 hours the reaction was quenched with water and extracted with ethyl acetate (4x). The organic phases were combined, dried (MgSO$_4$), filtered and concentrated. The residue was subjected to flash chromatography (hexane followed with 1% ethyl acetate) to afford 0.35 g (37%) of 2-(1-butoxy)thiazole as an amber oil.

n-BuLi (1.79 mmol, 1.1 mL, 1.6M) was added dropwise to a −78° C. solution of 2-(1-butoxy)thiazole (0.27 g, 1.7 mmol) in dry THF (15 mL). The solution was stirred for 1 h at −78° C., then SO$_2$ gas was bubbled over the surface of the solution for 10 min. The solution was warmed to rt, then the solvent was removed and the residue taken up in CH$_2$Cl$_2$ (15 mL) and NCS (0.24 g, 1.79 mmol) was added. After stirring at rt for 30 minutes, the solution was filtered and the filtrate concentrated. The residue was dissolved in acetone (15 mL) and NH$_4$OH ( 3.4 mL) was added. After 5 min, the acetone was removed in vacuo and the aqueous extracted with EtOAc, dried (MgSO$_4$) and concentrated. The residue was purified by flash chromatography using 25% EtOAc/hexane to give 0.26 g (65%) of 2-(1-butoxy)-5-thiazole sulfonamide.
$^1$H NMR (CD$_3$)$_2$CO:
7.54 (s, 1H), 6.98 (brs, 2H), 4.48 (t, 2H, J=6.5 Hz), 1.74–1.83 (m, 2H), 1.42–1.49 (m, 2H), 0.95 (t, 3H, J=7.3 Hz)
$^{13}$C NMR (CD$_3$)$_2$SO:
177.91, 141.17, 133.00, 73.37, 31.29, 19.48, 13.83
Mass Spect.:
EI-236 (M$^+$)
High Res.:
Calcd. 236.02893
Found 236.0287
Elemental Analysis:
Calcd. C 35.58, H 5.12, N 11.85
Found C 35.63, H 5.12, N 11.81

Example 35:

2-(1-Hexynyl)-5-thiazole sulfonamide

2-Bromothiazole (6.09 mmol, 1.0 g) was added to 40 mL of acetonitrile. CuI (1.52 mmol, 0.29 g), triethylamine (7.31 mmol, 1.01 mL) and bistriphenylphosphine palladium chloride (0.3 mmol, 0.21 g) were added and the solution degassed. Hexyne (6.09 mmol, 0.7 mL) was added and the mixture heated at refluxed overnight. Water was added followed by NaCl and ether. The layers were separated and the aqueous layer extracted with ether (4x). The organic layers were combined, dried (MgSO$_4$), filtered and concentrated. The residue was subjected to flash chromatography (10% ethyl acetate/hexane) to afford 0.36 g (36%) of 2-(1-hexynyl)thiazole.

n-BuLi (2.1 mmol, 1.3 mL, 1.6M) was added dropwise to a −78° C. solution of 2-(1-hexynyl)thiazole (0.33 g, 2.0 mmol) in dry THF (20 mL). The solution was stirred for 1 h at −78° C., then SO$_2$ gas was bubbled over the surface of the solution for 10 min. The solution was warmed to rt, then the solvent was removed and the residue taken up in CH$_2$Cl$_2$ (20 mL) and NCS (0.28 g, 2.10 mmol) was added. After stirring at rt for 1 hour, the solution was filtered and the filtrate concentrated. The residue was dissolved in acetone (20 mL) and NH$_4$OH (4 mL) was added. After 10 min., the acetone was removed in vacuo and the aqueous extracted with EtOAc, dried (MgSO$_4$) and concentrated. The residue was purified by flash chromatography using 30% EtOAc/hexane to give 0.27 g (56%) of 2-(1-hexynyl)-5-thiazole sulfonamide.
$^1$H NMR (CD$_3$)$_2$CO:
8.1 (s, 1H), 7.25 (brs, 2H), 2.55 (t, 2H, J=7 Hz), 1.61 (m, 2H), 1.48 (m, 2H), 0.93 (t, 3H, J=7.2 Hz)
$^{13}$C NMR (CD$_3$)$_2$SO:
153.20, 145.74, 142.27, 100.04, 74.09, 30.50, 22.51, 19.38, 13.70
Mass Spect.:
EI-244 (M$^+$)
High Res.:
Calcd. 244.0340
Found 244.0352
Elemental Analysis:
Calcd. C 44.24, H 4.95, N 11.47
Found C 44.30, H 4.92, N 11.38

Example 36:

2-(1-Hexyl)-5-thiazole sulfonamide 2-(1-hexynyl)-5-thiazole sulfonamide (0.04 g, 0.16 mmol) was dissolved in 5 mL of methanol. 0.01 g of palladium/carbon was added and the solution purged three times with hydrogen. The reaction was left under 30 psi of hydrogen for 48 hours. The mixture was filtered through celite and the filtrate concentrated. The residue was purified on the chromatatron (eluted with 5:1.5:3.5 $CH_2Cl_2$/Et$_2$O, hexane) to afford 32 mg (80%) of 2-hexyl-5-thiazole sulfonamide.

$^1$H NMR $(CD_3)_2CO$:
7.98 (s, 1H), 7.07 (brs, 2H), 3.03 (t, 2H, J=7.7 Hz), 1.78 (m, 2H), 1.32 (m, 4H), 0.87 (t, 3H, J=6.8 Hz)
$^{13}$C NMR $(CD_3)_2SO$:
176.92, 145.28, 141.24, 33.98, 32.08, 30.31, 29.22, 23.09, 14.23
Elemental Analysis:
Calcd. C 43.52, H 6.49, N 11.28
Found C 43.62, H 6.68, N 11.18

Example 37:

2-Phenyl-5-thiazole sulfonamide

2-Bromothiazole (1.2 mmol, 0.11 mL) and phenylboric acid (1.2 mmol, 0.146 g) were added to a solution of potassium carbonate (2M, 1.2 mL) and ethanol (0.6 mL) in deoxygenated toluene (12 mL). The resulting mixture was degassed for 30 minutes, then tetrakistriphenylphosphine palladium (0.036 mmol, 0.042 g) was added and the solution heated at reflux for 48 hours. The solids were removed by filtration and the solution extracted with toluene (5x), dried ($MgSO_4$), filtered and concentrated. The residue was subjected to flash chromatography (hexane followed with 5% ethyl acetate/hexane and then 10% ethyl acetate/hexane) to afford 0.13 g (69%) of 2-phenylthiazole.

n-BuLi (0.86 mmol, 0.54 mL, 1.6M) was added dropwise to a −78° C. solution of 2-phenylthiazole (0.13 g, 0.82 mmol) in dry THF (8 mL). The solution was stirred for 1 h at −78° C., then $SO_2$ gas was bubbled over the surface of the solution for 10 min. The solution was warmed to rt, then the solvent was removed and the residue taken up in $CH_2Cl_2$ (8 mL) and NCS (0.11 g, 0.86 mmol) was added. After stirring at rt for 2 hour, the solution was filtered and the filtrate concentrated. The residue was dissolved in acetone (1 mL) and $NH_4OH$ (1.6 mL) was added. After 10 min, the acetone was removed in vacuo and the aqueous extracted with EtOAc, dried ($MgSO_4$) and concentrated. The residue was purified by flash chromatography using 30% EtOAc/hexane to give 0.093 g (47%) of 2-phenyl-5-thiazole sulfonamide. m.p. 209°–210° C.

$^1$H NMR $(CD_3)_2CO$:
8.20 (s, 1H), 8.03 (m, 2H), 7.55 (m, 3H), 7.21 (brs, 2H)
$^{13}$C NMR $(CD_3)_2SO$:
172.63, 146.50, 141.76, 133.36, 132.20, 130.11, 127.48
Mass Spect.:
EI-240 (M$^+$)
High Res.:
Calcd. 240.0027
Found 240.0025
Elemental Analysis:
Calcd. C 44.98, H 3.36, N 11.66
Found C 45.12, H 3.35, N 11.58

Example 38:

2-(2-(methoxymethoxy)ethanoyl-5-thiazole sulfonamide n-BuLi (9.96 mmol, 6.2 mL, 1.6M) was added dropwise to a −78° C. solution of diisopropylamine (1.4 mL, 9.96 mmol) in dry THF (20 mL). The solution was stirred for 10 min. at 0° C., then tributyltinhydride (9.96 mmol, 2.68 mL) was added and the solution stirred for 15 min. The solution was cannulated into a 0° C. solution of paraformaldehyde (9.96 mmol, 0.3 g) and the solution stirred at rt for 3 hours. The reaction was quenched with $NH_4Cl$ and extracted with pentane (4x), dried ($MgSO_4$), and concentrated. The crude material was dissolved in $CH_2Cl_2$ (40 mL), dimethylaniline (14.9 mmol, 1.9 mL) was added and the solution cooled to 0° C. Chloromethylmethylether (14.9 mmol, 1.13 mL) was added and the reaction stirred for 2 hours. The reaction was diluted with pentane and then washed with cold 0.5M HCl, water, saturated $NaHCO_3$ and dried ($Na_2SO_4$). Flash chromatography (25% $CH_2Cl_2$/hexane) affords 1.49 g (41%) of (methoxymethoxymethyl)tributyl tin.

n-BuLi (2.87 mmol, 1.8 mL, 1.6M) was added dropwise to a −78° C. solution of (methoxymethoxymethyl)tributyl tin (1.05 g, 2.87 mmol) in dry THF (10 mL). After stirring for 30 minutes a solution of 2-formylthiazole (2.73 mmol, 0.31 g) in THF (2 mL) was added and the solution stirred overnight. The reaction was diluted with water and extracted with ethyl acetate, dried ($MgSO_4$), filtered and concentrated. The residue was subjected to flash chromatography (45% ethyl acetate/hexane) to afford 0.18 g (34%) of 2-(1-hydroxy- 2-(methoxymethoxy)ethyl)thiazole.

A mixture of 2-(1-hydroxy- 2-(methoxymethoxy)ethyl)thiazole (0.93 mmol, 0.18 g), TBSCl (1.1 mmol, 0.17 g) and DBU (1.1 mmol, 0.16 mL) in THF (1 mL) was stirred at rt overnight. The reaction was diluted with water and extracted with ethyl ether, dried ($MgSO_4$), filtered and concentrated. The residue was subjected to flash chromatography (10% ethyl acetate/hexane) to afford 0.20 g (70%) of 2-(1-(t-butyldimethylsiloxy)- 2-(methoxymethoxy)ethyl)thiazole.

n-BuLi (0.68 mmol, 0.42 mL, 1.6M) was added dropwise to a −78° C. solution of 2-(1-(t-butyldimethylsiloxy)-2-(methoxymethoxy)ethyl)thiazole (0.20g, 0.65 mmol) in dry THF (6 mL). The solution was stirred for 1 h at −78° C., then $SO_2$ gas was bubbled over the surface of the solution for 10 min. The solution was warmed to rt, then the solvent was removed and the residue taken up in $CH_2Cl_2$ (6 mL) and NCS (0.42 g, 0.68 mmol) was added. After stirring at rt for 2 hour, the solution was filtered and the filtrate concentrated. The residue was dissolved in acetone (2 mL) and $NH_4OH$ (1.3 mL) was added. After 15 min., the acetone was removed in vacuo and the aqueous extracted with EtOAc, dried ($MgSO_4$) and concentrated. The residue was taken up in THF (6 mL) and treated with TBAF (0.78 mmol, 0.78 mL) for 30 minutes at rt. Water was added and the solution extracted with ethyl acetate, dried ($MgSO_4$), filtered and concentrated. The residue was subjected to flash chromatography (70% ethyl acetate/hexane) to afford 86 mg (49%) of 2-(1-hydroxy- 2-(methoxymethoxy)ethyl)-5-thiazole sulfonamide.

Jones' reagent (0.14 mL, 0.39 mmol, 2.67M) was added dropwise to a 0° C. solution of 2-(1-hydroxy- 2-(methoxymethoxy)ethyl)-5-thiazole sulfonamide (0.086 g, 0.32 mmol) in acetone (1 mL). The ice bath was removed and the solution stirred for 15 min. The reaction was incomplete an additional 0.07 mL of Jones' reagent was added and the reaction stirred for 15 more minutes. The reaction was quenched with a few drops of isopropanol and the acetone removed in vacuo. The residue was taken up in water and extracted with EtOAc. The combined extracts were dried ($MgSO_4$), concentrated and purified by flash chromatography using 55% EtOAc/hexane to give 4.8 mg (5.3%) of 2-(2-(methoxymethoxy)ethanoyl)-5-thiazole sulfonamide.

$^1$H NMR $(CD_3)_2CO$:
8.35 (s, 1H), 7.39 (brs, 2H), 5.03 (s, 2H), 4.72 (s, 2H), 3.35 (s, 3H)

$^{13}$C NMR (CD$_3$)$_2$SO:
190.19, 168.57, 146.82, 146.69, 97.30, 97.23, 69.68, 69.61, 55.75, 55.64
Mass Spect.:
EI-267 (MH$^+$)
High Res.:
Calcd. 267.0119 (MH$^+$)
Found 267.0119

Example 39:

b 2-(N-t-butylsulfamyl)-5-thiazole sulfonamide

To a solution of 2-N-t-butylthiazole sulfonamide (0.5 g, 2.3 mol) in 23 mL of THF at −78° C. was added n-butyllithium (1.6M, 2.9 mL, 4.6 mmol). The reaction was stirred under argon at −78° C. for 60 min. An excess of SO$_2$ was bubbled through the reaction. The reaction was slowly warmed to rt and then concentrated under reduced pressure. The crude product was added to 35 mL of dichloromethane. N-chlorosuccinamide ( 0.34 g, 2.53 mmol) was added and the reaction stirred at rt for 60 min. The mixture was filtered and the filtrate collected and concentrated under reduced pressure. To the crude product in 30 mL of acetone was added 2 ml of concentrated ammonium hydroxide in 10 mL of acetone. The reaction was acidified with 1N HCl and then extracted with ethyl acetate. The organic phase was washed with water and then brine. The solvent was removed under reduced pressure and the product subjected to flash chromatography (1:1 hexane/ethyl acetate). 0.27g (0.9 mmol, 39%) of 2-(N-t-butylsulfamyl)-5-thiazole sulfonamide (white crystals) was recovered.
$^1$H NMR (CD$_3$)$_2$CO:
8.29 (s, 1H), 7.35 (bs, 3H), 1.32 (s, 9H)
$^{13}$C NMR (CD$_3$)$_2$CO:
173.3, 146.7, 146.0, 56.1, 30.2
Mass Spect.:
EI-300 (MH$^+$)
High Res.:
Calcd. 283.9833 (M—CH$_3$)
Found 283.9833 (M—CH$_3$)
Elemental Analysis:
Calcd. C 28.09, H 4.35, N 14.05
Found C 28.17, H 4.12, N 14.10

Example 40:

2-(N-Methyl-N-(dimethylamino)ethyl)sulfamyl-5-thiazole sulfonamide

To a solution of 2-bromothiazole (5.0 g, 0.03 mol) in 122 mL of ethyl ether at −78° C. was added n-butyllithium (1.6M, 19.1 mL, 0.03 mmol). The reaction was stirred under argon at −78° C. for 60 min. An excess of SO$_2$ was bubbled through the reaction. The reaction was slowly warmed to rt and then concentrated under reduced pressure. The crude product was added to 125 mL of dichloromethane. N-chlorosuccinamide (4.5 g, 0.033 mmol) was added and the reaction stirred at rt for 30 min. The mixture was filtered and the filtrate collected and concentrated under reduced pressure. To the crude product in 22 mL of THF was added trimethylethylene diamine (5.5 mL, 0.15 mmol). The reaction was stirred at rt for 15 min. and then quenched with water. The organic phase was washed with water (3X) followed by brine. The solvent was removed under reduced pressure and the product subjected to flash chromatography (10:1 chloroform/methanol). 1.1 g of 2-(N-methyl-N-(dimethylamino)ethyl)sulfamyl thiazole was recovered.

To a solution of 2-(N-methyl-N-(dimethylamino)ethyl)sulfamyl thiazole (1.1 g, 4.42 mmol) in 44 mL of THF at −78° C. was added n-butyllithium (1.6M, 2.8 mL, 4.42 mmol). The reaction was stirred under argon at −78° C. for 60 min. An excess of SO$_2$ was bubbled through the reaction. The reaction was slowly warmed to rt and then concentrated under reduced pressure. The crude product was added to 44 mL of dichloromethane. N-chlorosuccinamide (0.65 g, 4.86 mmol) was added and the reaction stirred at rt for 2 h. An additional 0.65 g of N-chlorosuccinamide was added and the reaction stirred at rt for another 30 min. The mixture was filtered and the filtrate collected and concentrated under reduced pressure. To the crude product in 50 mL of acetone was added 5 mL of concentrated ammonium hydroxide in 10 mL of acetone. Upon completion the reaction was diluted with water and extracted with ethyl acetate. The organic phase was washed with water (3X) followed by brine. The solvent was removed under reduced pressure and the product subjected to flash chromatography (4:1 chloroform/methanol). 0.25 g (0.76 mmol, 17%) of 2-(N-methyl-N-(dimethylamino)ethyl)sulfonyl-5-thiazole sulfonamide (tan crystals) was recovered.
$^1$H NMR (CD$_3$)$_2$CO:
8.32(s, 1H), 7.40 (bs, 2H), 3.41 (t, J=6.2 Hz, 2H), 3.08 (s,3H), 2.45 (t, J=6.2 Hz, 2H), 2.10 (s, 6H)
$^{13}$C NMR (CD$_3$)$_2$CO:
169.4, 146.4, 146.3, 57.5, 49.3, 45.4, 36.1
Mass Spect.:
CI-329 (MH$^+$)
High Res.:
Calcd. 329.0412
Found 329.0424
Elemental Analysis:
Calcd. C 29.27, H 4.88, N 17.07
Found C 29.42, H 4.73, N 16.95

Example 41:

4-Methyl-1-( 2-sulfamylthiazolyl)sulfonyl)piperazine

To a solution of 2-thiazole sulfonylchloride (4.0 g, 0.022 mol) in 80 mL of THF at rt was added N-methyl piperazine (2.9 mL, 0.026 mol) in 10 mL of THF. The reaction was stirred for 10 min. and then diluted with ethyl acetate. The reaction was washed with water (3X) followed by brine. The solvent was removed under reduced pressure and the product subjected to flash chromatography (20:1 chloroform/methanol). 0.92 g of 2-thiazoylsulfonyl piperazine was recovered.

To a solution of 2-thiazoylsulfonyl piperazine (0.92 g, 3.7 mmol) in 37 mL of THF at −78° C. was added n-butyllithium (2.3 mL, 3.7 mmol). The solution was stirred under argon at −78° C. for 60 min. An excess of SO$_2$ was bubbled through the reaction. The reaction was slowly warmed to rt and then concentrated under reduced pressure. The crude product was added to 40 mL of dichloromethane. N-chlorosuccinamide (0.54 g, 4.1 mmol) was added and the reaction stirred at rt for 1.5 h. The mixture was filtered and the filtrate collected and concentrated under reduced pressure. To the crude product in 40 mL of acetone was added 3 mL of concentrated ammonium hyroxide in 10 mL of acetone. Upon completion the reaction was diluted with water and extracted with ethyl acetate. The organic phase was washed with water (3X) followed by brine. The solvent was removed under reduced pressure and the product subjected to flash chromatography (4:1 chloroform/methanol). 40 mg (0.12 mmol, 3.3%) of 4-methyl-1-(2-( 5-sulfamylthiazoyl)sulfonyl)piperazine (tan crystals) was recovered.

$^1$H NMR $(CD_3)_2CO$:

8.39 (s, 1H), 7.42 (bs, 2H), 3.32 (t, J=5 Hz, 4H), 2.45 (t, J=5 Hz, 4H), 2.23 (s, 3H)

$^{13}$C NMR $(CD_3)_2CO$:

7.43, 147.26, 146.70, 54.67, 47.24, 45.87

Mass Spect.:

CI-327 (MH$^+$)

High Res.;

Calcd. 327.0255

Found 327.0233

Elemental Analysis:

Calcd. C 29.45, H 4.29, N 17.18

Found C 29.53, H 4.17, N 17.14

The compounds of the invention were assayed for biological activity as follows:

1. Carbonic anhydrase activity was assayed according to the micromethod of Maren (*J. Pharmacol. Exptl. Therap.*, 130, 26– 29, 1960). All solutions and reagents were maintained at 0°–4° C. The final assay mixture contained 16 mM phenol red, added enzyme and 62.5 mM sodium carbonate/bicarbonate. Its volume was kept constant at 0.8 mL. The time required for the added enzyme to lower the pH of CO 2-saturated carbonate/bicarbonate buffer from pH 9.9 to 6.8 was measured using the color change of phenol red as endpoint. T1 is the time recorded for the reaction containing no enzyme. T2 is the time recorded for the reaction containing pure CA11 enzyme from human erythrocyte, or an unknown amount in a sample. Enzyme activities (unit) were calculated using the formula:

Unit/ug=$(T_1-T_2)(T_2*$ug protein used in assay)

IC$_{50}$ of a carbonic anhydrase inhibitor is the concentration that lowers the enzyme activity to half.

The results of this assay are reported in Table 1, below.

TABLE I

| Name of structure | IC$_{50}$ in nM | Cysteine reactivity |
| --- | --- | --- |
| 2-Thiazole sulfonamide | 61 nM | N.R. |
| 5-Benzoyl-2-thiazole sulfonamide | 5 nM | reactive |
| 5-Phenylsulfonyl-2-thiazole sulfonamide | 6 nM | reactive |
| 5-(Phenylthio)-2-thiazole sulfonamide | 2.7 nM | 0.005 |
| 5-Chloro-2-thiazole sulfonamide | 5.9 nM | 0.00002 |
| 5-(Ethylthio)-2-thiazole sulfonamide | 4.2 nM | 0.000024 |
| 5-(2-Hydroxyethylthio)-2-thiazole sulfonamide | 6.6 nM | — |
| 4-Methyl-2-thiazole sulfonamide | 120 nM | 0.00005 |
| 4-Carboethoxy-2-thiazole sulfonamide | 77 nM | <0.000005 |
| 5-(4-Acetoxybutanoyl)-2-thiazole sulfonamide | 8.4 nM | reactive |
| 5-Ethylsufinyl-2-thiazole sulfonamide | 11.4 nM | reactive |
| 5-Bromo-2-thiazole sulfonamide | 7.8 nM | — |
| 5-Methyl-4-phenyl-2-thiazole sulfonamide | 84 nM | N.R. |
| 2-Sulfamyl-4,5,6,7-tetrahydrobenzothiazole | 15 nM | — |
| 5-(1-Hexynyl)-2-thiazole sulfonamide | 5.6 nM | 0.00019 |
| 5-Phenyl-2-thiazole sulfonamide | 6 nM | — |
| 4-Phenyl-2-thiazole sulfonamide | 20 nM | — |
| 5-(2-Carbomethoxyethylthio)-2-thiazole sulfonamide | 9.1 nM | — |
| 5-Benzyloxycarbonyl-2-sulfamyl-4,5,6,7-tetrahydrothiazole[5,4-c]pyridine | 11 nM | — |
| 5-Chloro-4-(4-methoxyphenyl)-2-thiazole sulfonamide | 30 nM | — |
| 5-Benzyl-2-thiazole sulfonamide | 9.3 nM | — |
| 4-(4-Methoxyphenyl)-2-thiazole sulfonamide | 33 nM | — |

TABLE I-continued

| Name of structure | IC$_{50}$ in nM | Cysteine reactivity |
| --- | --- | --- |
| 2-(1-Hydroxyhexyl)-5-thiazole sulfonamide | 10 nM | — |
| 2-(Ethylthio)-5-thiazole sulfonamide | 6.3 nM | <0.0000024 |
| 2-(Ethylsulfonyl)-5-thiazole sulfonamide | 6.7 nM | reactive |
| 2-(Phenylsulfonyl)-5-thiazole sulfonamide | 5.5 nM | reactive |
| 2-Hexanoyl-5-thiazole sulfonamide | 3.5 nM | 0.00007 |
| 2-Phenylthio-5-thiazole sulfonamide | 5.5 nM | N.R. |
| 2-Cyclopropylcarbonyl-5-thiazole sulfonamide | 3.5 nM | <0.000024 |
| 2-(N-t-butylsulfamyl)-5-thiazole sulfonamide | 5.3 nM | — |
| 2-(N-Methyl-N-(dimethylamino)-ethyl)sulfamyl-5-thiazole sulfonamide | 14.5 nM | reactive |
| 2-(1-Keto-2-methoxymethoxymethyl)-5-thiazole sulfonamide | 10.3 nM | — |
| 1-(2-(-Sulfamylthiazolyl)sulfonyl)-4-methyl-piperazine | 9.3 nM | reactive |
| (2-(5-Sulfamylthiazolyl))(phenyl)-sulfoxide | 12.7 nM | reactive |
| 2-(4-(N,N-Dimethylamino)butanoyl)-5-thiazole sulfonamide hydrochloride | 26 nM | — |
| 2-(1-Butoxy)-5-thiazole sulfonamide | 16 nM | <0.00005 |
| 2-(1-Hexynyl)-5-thiazole sulfonamide | 7.7 nM | 0.001 |
| 2-Phenyl-5-thiazole sulfonamide | 20 nM | — |
| 2-Hexyl-5-thiazole sulfonamide | 20.6 nM | — |

2. Cysteine reactivity was measured by the following probe assay procedure. Three stock solutions of: A) the CAI compound to be tested in 50 nM phosphate buffer; B) cysteine (10 nM) in 50 mM phosphate buffer at pH 7.4; and C) phosphate buffer (50 mM) at pH 7.4, were prepared. Each solution was deoxygenated by bubbling with N$_2$ for 10–15 min.

Reaction mixtures were prepared in triplicate by mixing equal volumes (1 mL) of two stock solutions as follows:

I) A+B at 4° C.

II) A+B at RT

III) A+C at RT

Hydrolytic or other chemical reactivity was detected by comparison of solutions I and II. Cysteine related reactions were detected by comparison of solutions II and III. All samples were assayed using HPLC under constant conditions and over a short period of time to minimize experimental variations in peak heights not related to CAI concentration differences. Each of the three solutions were assayed in sequence to give three sets of experimental values: Ia, IIa, IIIa, Ib, IIb, IIIb, Ic, IIc, IIIc and each set was compared separately. Mean and standard deviations of the three sets were recorded.

While particular embodiments of the invention have been described it will be understood of course that the invention is not limited thereto since many obvious modifications can be made and it is intended to include within this invention any such modifications as fall within the scope of the appended claims.

Having now described the invention, what is claimed is:

1. A compound having the formula:

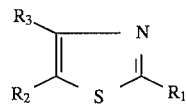

wherein R$_1$ is:

—SO$_2$NH$_2$; —S(O)$_n$R$_4$; —OR$_4$; phenyl, benzyl; phenethyl; styryl; pyridyl; alkyl having from 1 to 8 carbon atoms, or alkenyl or alkynyl having from 2 to 8 carbon atoms which can optionally be substituted with one or more hydroxy or carboxy groups wherein $R_4$ is:

hydrogen; alkyl having from 1 to 6 carbon atoms or alkenyl or alkynyl having from 2 to 6 carbon atoms optionally substituted by dimethylamine; alicyclic having from 3 to 6 carbon atoms; carbalkoxyalkyl having 1 to 4 carbon atoms in the carbonyl moiety and from 1 to 6 carbon atoms in the alkoxy moiety; phenyl; $CH_3OCH_2OCH_2$; lower dialkylamino optionally further substituted by dimethylamine; or saturated nitrogen-containing heterocycles containing from 5 to 7 atoms optionally substituted with alkyl having from 1 to 3 carbon atoms and n is 0, 1 or 2;

$R_2$ is:

—$SO_2NH_2$; —$S(O)_nR_4$; —$C(O)R_4$; —$OR_4$; bromo; chloro; phenyl; pyridyl; furanyl; thiophenyl; alkyl having from 1 to 8 carbon atoms, or alkenyl or alkynyl having from 2 to 8 carbon atoms which can optionally be substituted with one or more hydroxy groups, wherein $R_4$ and n are as defined above;

$R_3$ is:

hydrogen; or $R_2$ and $R_3$ taken together form a ring fused with the 4–5 positions of the thiazole ring and are chosen from the group consisting of tetrahydrobenzene, tetrahydropyridine and thiopyran and can optionally be substituted by carboxylic acid, lower alkyl or benzyl esters of carboxylic acid, lower alkyl, or halogen; provided that at least one of $R_1$ and $R_2$ must represent the sulfonamide moiety, —$SO_2NH_2$ and that $R_2$ cannot be chloro or bromo when $R_3$ is methyl, carboxylic acid or esters thereof, or unsubstituted phenyl.

2. The compound of claim 1 wherein $R_1$ is primary sulfonamide, $R_2$ is as defined in claim 1 and $R_3$ is hydrogen.

3. The compound of claim 1 wherein $R_1$ is as defined in claim 1, $R_2$ is primary sulfonamide and $R_3$ is hydrogen.

4. The compound of claim 1 wherein $R_2$ and $R_3$, together, represent the optionally substituted ring fused to the thiazole ring and $R_1$ is primary sulfonamide.

5. The compound of claim 3 wherein $R_1$ is —$S(O)_nR_4$, —$C(O)R_4$, benzyl, —$CH=CHR_4$, or —$C=CR_4$ wherein $R_4$ is chosen from the group consisting of phenyl, a straight or branched carbon chain of up to 6 atoms, and alicycles of 3 to 6 carbon atoms.

6. The compound of claim 1 having the following structure:

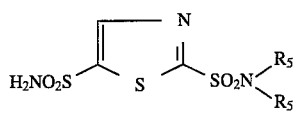

wherein each $R_5$ independently is chosen from the group consisting of hydrogen, alkyl of 1 to 6 carbon atoms; phenyl; lower dialkylamino optionally further substituted by dimethylamine, and saturated nitrogen-containing heterocycles containing from 5 to 7 atoms optionally substituted with alkyl having from 1 to 3 carbon atoms.

7. The compound of claim 1 wherein $R_1$ is —$SO_2NH_2$ and $R_2$ is chosen from the group consisting of phenylthio, ethylthio, chloro, bromo, 2-hydroxyethylthio, 1-hexynyl, phenyl, benzyl and 2-carbomethoxyethylthio, and $R_3$ is hydrogen.

8. The compound of claim 1 wherein $R_2$ is —$SO_2NH_2$ and $R_1$ is chosen from the group consisting of phenylthio, ethylthio, cyclopropylketo, 1-hexynyl, 1-hydroxyhexyl and hexanoyl, and $R_3$ is hydrogen.

9. A method of treating the elevated intraocular pressure of a patient which comprises administering to said patient an effective amount of a compound having the formula:

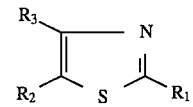

wherein $R_1$ is: —$SO_2NH_2$; —$S(O)_nR_4$; —$C(O)R_4$; —$OR_4$; phenyl, heteroaryl, aralkyl, heteroaralkyl, aralkenyl or heteroaralkenyl having from 5 to 6 atoms in the aryl moiety and 1 to 2 carbon atoms in the alkyl or 2 carbon atoms in the alkenyl moiety; alkyl having from 1 to 8 carbon atoms, or alkenyl or alkynyl having from 2 to 8 carbon atoms which can optionally be substituted with one or more hydroxy or carboxy groups wherein $R_4$ is: hydrogen; alkyl having from 1 to 6 carbon atoms or alkenyl or alkynyl having from 2 to 6 carbon atoms; alicyclic having from 3 to 6 carbon atoms; lower carbalkoxyalkyl; phenyl; $CH_3OCH_2OCH_2$; lower dialkylamino optionally further substituted by dimethylamine; or saturated nitrogen-containing heterocycles containing from 5 to 7 atoms optionally substituted with alkyl having from 1 to 3 carbon atoms and n is 0, 1 or 2;

$R_2$ is: —$SO_2NH_2$; —$S(O)_nR_4$; —$C(O)R_4$; —$OR_4$; hydrogen; bromo; chloro; aryl or heteroaryl having from 5 to 6 atoms; alkyl having from 1 to 8 carbon atoms, or alkenyl or alkynyl having from 2 to 8 carbon atoms which can optionally be substituted with one or more hydroxy groups wherein $R_4$ and n are as defined above;

$R_3$ is: hydrogen; alkyl of 1 to 6 carbon atoms; carboxy; carboxy alkyl of 1 to 4 carbon atoms; or phenyl optionally mono- or di-substituted with lower alkoxy, fluoro, chloro, bromo or alkyl of 1 to 3 carbon atoms; or $R_2$ and $R_3$ taken together form a ring fused with the 4–5 positions of the thiazole ring and are chosen from the group consisting of tetrahydrobenzene, tetrahydropyridine and thiopyran and can optionally be substituted by carboxylic acid, lower alkyl or benzyl esters of carboxylic acid, lower alkyl, or halogen; provided that at least one of $R_1$ and $R_2$ must represent the sulfonamide moiety, —$SO_2NH_2$, and pharmaceutically acceptable salts and mixtures thereof.

10. The method of claim 9 which comprises topically administering said compound to the eye.

11. A method of treating the elevated intraocular pressure of glaucoma in a patient which comprises administering to said patient an effective amount of a compound according to claim 9.

12. The method of claim 11 which comprises topically administering to the eye said compound of claim 8.

13. The method of claim 12 which comprises administering a unit it dosage of from 0.001 to 10.0 mg of the compound of claim 8 on a daily basis.

14. A pharmaceutical composition for treating a patient having glaucoma, by topical administration to the eye, which comprises an effective amount of a compound according to claim 1 in a pharmaceutically-acceptable carrier.

15. The composition of claim 14 comprising from 0.01 to 15% of said compound of claim 1.

16. A method of inhibiting carbonic anhydrase activity in a patient which comprises administering to said patient an effective amount of a compound according to claim 1.

17. The method of claim 16 which comprises topically administering to the eye said compound of claim 1.

18. The method of claim 17 which comprises administering a unit dosage of from 0.001 to 10.0 mg of the compound of claim 1 on a daily basis.

* * * * *